United States Patent
Zhu et al.

(10) Patent No.: US 11,769,908 B2
(45) Date of Patent: *Sep. 26, 2023

(54) LITHIUM AND SODIUM SUPERIONIC CONDUCTORS

(71) Applicant: The Regents of the University of California, Oakland, CA (US)

(72) Inventors: Zhuoying Zhu, La Jolla, CA (US); Shyue Ping Ong, La Jolla, CA (US); Erik Wu, La Jolla, CA (US); Han Nguyen, La Jolla, CA (US); Ying Shirley Meng, La Jolla, CA (US); Iek Heng Chu, La Jolla, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/528,280

(22) Filed: Nov. 17, 2021

(65) Prior Publication Data
US 2022/0223906 A1 Jul. 14, 2022

Related U.S. Application Data

(62) Division of application No. 16/346,144, filed as application No. PCT/US2017/059340 on Oct. 31, 2017, now Pat. No. 11,201,349.
(Continued)

(51) Int. Cl.
*H01M 10/0562* (2010.01)
*H01M 4/38* (2006.01)
(Continued)

(52) U.S. Cl.
CPC ........ *H01M 10/0562* (2013.01); *G16C 20/00* (2019.02); *G16C 20/30* (2019.02);
(Continued)

(58) Field of Classification Search
CPC .. H01M 10/0562; H01M 4/381; H01M 4/382; H01M 10/052; H01M 10/054;
(Continued)

(56) References Cited

U.S. PATENT DOCUMENTS

| 7,491,458 B2 * | 2/2009 | Visco | H01M 12/04 |
| | | | 429/246 |
| 7,608,178 B2 | 10/2009 | De Jonghe | |

(Continued)

OTHER PUBLICATIONS

Xiaojun Zhao, Rapid Hierarchical Screening for Promising Ternary and Quaternary Inorganic Solid-State Electrolytes, 2022, 10 pages (Year: 2022).*

(Continued)

*Primary Examiner* — Tung S Lau
(74) *Attorney, Agent, or Firm* — MAYER & WILLIAMS, PC; Stuart H. Mayer

(57) ABSTRACT

Presented are new, earth-abundant lithium superionic conductors, $Li_3Y(PS_4)_2$ and $Li_5PS_4Cl_2$, that emerged from a comprehensive screening of the Li—P—S and Li-M-P—S chemical spaces. Both candidates are derived from the relatively unexplored quaternary silver thiophosphates. One key enabler of this discovery is the development of a first-of-its-kind high-throughput first principles screening approach that can exclude candidates unlikely to satisfy the stringent $Li^+$ conductivity requirements using a minimum of computational resources. Both candidates are predicted to be synthesizable, and are electronically insulating. Systems and methods according to present principles enable new, all-solid-state rechargeable lithium-ion batteries.

9 Claims, 20 Drawing Sheets

Related U.S. Application Data

(60) Provisional application No. 62/547,478, filed on Aug. 18, 2017, provisional application No. 62/415,167, filed on Oct. 31, 2016.

(51) Int. Cl.
| | | |
|---|---|---|
| *H01M 10/052* | (2010.01) | |
| *H01M 10/054* | (2010.01) | |
| *G16C 20/30* | (2019.01) | |
| *G16Z 99/00* | (2019.01) | |
| *G16C 20/00* | (2019.01) | |

(52) U.S. Cl.
CPC ............ *G16Z 99/00* (2019.02); *H01M 4/381* (2013.01); *H01M 4/382* (2013.01); *H01M 10/052* (2013.01); *H01M 10/054* (2013.01); *H01M 2300/0068* (2013.01)

(58) Field of Classification Search
CPC ........... H01M 2300/0068; G16C 20/00; G16C 20/30; G16Z 99/00
See application file for complete search history.

(56) References Cited

U.S. PATENT DOCUMENTS

| | | | | |
|---|---|---|---|---|
| 7,998,617 | B2 * | 8/2011 | Armand | H01M 4/136 |
| | | | | 429/221 |
| 8,334,075 | B2 | 12/2012 | Visco | |
| 8,361,664 | B2 * | 1/2013 | Visco | H01M 16/003 |
| | | | | 429/491 |
| 9,123,941 | B2 * | 9/2015 | Visco | H01G 11/06 |
| 11,201,349 | B2 * | 12/2021 | Zhu | G16Z 99/00 |
| 11,527,774 | B2 * | 12/2022 | Read | H01G 11/02 |
| 2004/0002002 | A1 * | 1/2004 | Mizuta | H01M 10/052 |
| | | | | 429/188 |
| 2005/0100792 | A1 * | 5/2005 | Visco | H01M 12/08 |
| | | | | 429/231.95 |
| 2005/0175894 | A1 * | 8/2005 | Visco | H01M 4/366 |
| | | | | 429/212 |
| 2007/0048605 | A1 * | 3/2007 | Pez | H01M 10/0568 |
| | | | | 568/4 |
| 2008/0138704 | A1 * | 6/2008 | Mizuta | H01G 11/62 |
| | | | | 429/188 |
| 2009/0286114 | A1 | 11/2009 | Visco et al. | |
| 2011/0014522 | A1 | 1/2011 | Visco | |
| 2012/0270112 | A1 | 10/2012 | Visco | |
| 2013/0302704 | A1 | 11/2013 | Visco | |
| 2014/0057153 | A1 | 2/2014 | Visco | |
| 2015/0204809 | A1 | 7/2015 | Miara et al. | |
| 2016/0156064 | A1 | 6/2016 | Miyashita et al. | |
| 2016/0246153 | A1 | 8/2016 | Garcia | |

OTHER PUBLICATIONS

Mo et al., First Principles Study of the U10GeP2S12 Lithium Super Ionic Conductor Material, Chemistry of Materials, vol. 24, Dec. 9, 2011 [retrieved on Dec. 6, 2017]. Retrieved from the Internet: < URL: http://web.mit.edu/ceder/publications/Mo_Ionic_conductor_2012.pdf> pp. 15-17.

Zhu et al., Li3Y(PS4)2 and Li5PS4Cl2: New Lithium Superionic Conductors Predicted from Silver Thiophosphates using Efficiently Tiered Ab Initio Molecular Dynamics Simulations, Chemistry of Materials, Dec. 20, 2016 [retrieved on Dec. 6, 2017]. Retrieved from the Internet: < URL: https://materialsvirtuallab.org/pubs/10.1021 acs.chemmater.6b04049.pdf> entire document.

Zhuoying Zhu, Li3Y(PS4)2 and Li5PS4Cl2: New Lithium Superionic Conductors Predicted from Silver Thiophosphates using Efficiently Tiered Ab Initio Molecular Dynamics Simulations, Published: Dec. 20, 2016, 11 pages (Year: 2016).

Yifei Mo, First Principles Study of the Li10GeP2S12 Lithium Super Ionic Conductor Material, Dec. 8, 2011, 3 pages (Year: 2011).

Tina Chen, Evaluation of Mg Compounds as Coating Materials in Mg Batteries, 10 pages, Jan. 2019 (Year: 2019).

Zhuoying Zhu, 2019, Design and Optimization of Alkali Superionic Conductors for Solid-State Batteries using First-Principles Calculations, 24 pages (Year: 2019).

Aidong Zhou, Synthesis and Characterization of New Solid-State Li-Superionic Conductors, Laidong Zhou 2017, 99 pages (Year: 2017).

* cited by examiner

LITHIUM AND SODIUM SUPERIONIC CONDUCTORS

CROSS-REFERENCE TO RELATED APPLICATIONS

This application is a divisional of U.S. application Ser. No. 16/346,144, filed Apr. 30, 2019 entitled "LITHIUM AND SODIUM SUPERIONIC CONDUCTORS" which is a National Stage of PCT/US17/59340, filed Oct. 31, 2017 which claims the benefit of priority of U.S. Provisional Patent Application Ser. No. 62/415,167, filed Oct. 31, 2016, entitled "NOVEL LITHIUM SUPERIONIC CONDUCTOR SOLID ELECTROLYTES", and U.S. Provisional Patent Application Ser. No. 62/547,478, filed Aug. 18, 2017, entitled "NOVEL SODIUM SUPERIONIC CONDUCTOR SOLID ELECTROLYTE" both owned by the assignee of the present application and herein incorporated by reference in their entirety.

GOVERNMENT FUNDING

This invention was made with government support under DE-SC0012118 awarded by the Department of Energy and under CMM11436976 awarded by the National Science Foundation The government has certain rights in the invention

BACKGROUND

All-solid-state rechargeable lithium-ion batteries (ss-LIBs) are a revolutionary architecture for energy storage that holds the promise to be both more energy dense as well as safer than traditional organic-liquid-electrolyte-based lithium-ion batteries. The crucial enabling component in ss-LIBs is the non-flammable lithium superionic conductor solid electrolyte, which must possess a challenging suite of properties, including high $Li^+$ conductivity, excellent phase stability, electrochemical and mechanical compatibility with the electrodes, and ideally, stability under ambient air.

Thiophosphate lithium superionic conductors have emerged as one of the leading contenders for ss-LIB solid electrolyte applications. For instance, the $Li_{10}GeP_2S_{12}$ (LGPS) family of materials and the $Li_7P_3S_1$ glass-ceramic have ionic conductivities exceeding 10 mS/cm, on par or even exceeding that of organic solvent electrolytes. More recently, $Li_{9.54}Si_{1.74}P_{1.44}S_{11.7}Cl_{0.3}$, which also has the LGPS structure, was reported to have an ionic conductivity as high as 25 mS/cm at room temperature. Besides typically higher ionic conductivities, sulfides have the advantage of being softer than oxides, allowing low porosity and intimate electrode-electrolyte contact to be achieved via cold-pressing techniques.

Despite these advances, the number of known lithium superionic conductors remains relatively few, and existing materials all suffer from various limitations. For instance, $Li_0GeP_2S_{12}$ is expensive due to the use of Ge, while the Sn and Si substituted analogues tend to form conducting, non-passivating phases upon contact with the Li anode. Other candidates, such as $Li_7P_3S_{11}$, are metastable and tends to form non-passivating layers with the typical $LiCoO_2$ cathode used in today's LIBs. There is thus a need for the development of new lithium superionic conductors that can potentially mitigate some of these limitations.

SUMMARY

Systems and methods according to present principles meet the needs of the above in several ways.

Presented are new, earth-abundant lithium superionic conductors, $Li_3Y(PS_4)_2$ and $Li_5PS_4Cl_2$, that emerged from a comprehensive screening of the Li—P—S and Li-M-P—S chemical spaces. Both candidates are derived from the relatively unexplored quaternary silver thiophosphates. One key enabler of this discovery is the development of a first-of-its-kind high-throughput first principles screening approach that can exclude candidates unlikely to satisfy the stringent $Li^+$ conductivity requirements using a minimum of computational resources. Both candidates are predicted to be synthesizable, and are electronically insulating. Systems and methods according to present principles enable new, all-solid-state rechargeable lithium-ion batteries.

$Li_3Y(PS_4)_2$ may in some cases have superior properties. Compared to the existing lithium superionic conductors, $Li_3Y(PS_4)_2$, the more promising among the two, is expected to present an overall better balance of properties as a lithium superionic conductor electrolyte for all-solid-state battery applications. It has better predicted phase and electrochemical stability. Its $Li^+$ conductivity is sufficiently high (>2 mS/cm) such that it is not likely a limiting factor, and can be increased multi-fold to ~7 mS/cm via aliovalent doping strategies.

Regarding the new screening approach for superionic conductor electrolytes, its validity has been confirmed and the same has been shown to efficiently extract promising candidates with a minimal cost of computational resources.

In one aspect, the invention is directed towards a high-throughput screening method for superionic conductor, comprising: determining an initial pool of candidate structures from existing Li—P—S, Ag—P—S ternary and Li-M-P—S, Ag-M-P—S quaternary structures; filtering out unstable materials; and performing diffusivity screening on remaining materials.

Implementations of the invention may include one or more of the following. The filtering may be performed by phase stability analysis. The diffusivity screening may be performed by a three step approach. The three steps may include topological analysis, quick diffusivity estimation, and long AIMD simulations. The long AIMD simulations may be performed at multiple temperatures for a converged diffusivity of the most promising candidates. The method may further include performing dopant and composition optimization.

In another aspect, the invention is directed to a superionic conductor, found by the method described above.

In yet another aspect, the invention is directed to a superionic conductor, having the structures of $Li_3Y(PS_4)_2$ or $Li_5PS_4C_{12}$.

Advantages of certain implementations of the invention may include one or more of the following. Li superionic conductors as solid electrolytes have several advantages, including overcoming the potential leakage and flammability problems arising from use of traditional organic liquid electrolytes. The lithium superionic conductors according to present principles further exhibit high conductivity (>2 mS/cm), good phase and electrochemical stability and low electronic conductivity, which are highly promising to boost the electrochemical performance of all-solid-state battery applications.

In another aspect, the new screening approach for superionic conductor electrolytes has been employed to a predict a new Na superionic conductor ($Na_3Y(PS_4)_2$), which has excellent phase stability at 0 K and high conductivity (>10 mS/cm). It is the first sodium conductor from the computational or experimental side that exhibits both good phase stability and very high conductivity.

Other advantages will be understood from the description that follows, including the figures and claims.

This Summary is provided to introduce a selection of concepts in a simplified form. The concepts are further described in the Detailed Description section. Elements or steps other than those described in this Summary are possible, and no element or step is necessarily required. This Summary is not intended to identify key features or essential features of the claimed subject matter, nor is it intended for use as an aid in determining the scope of the claimed subject matter. The claimed subject matter is not limited to implementations that solve any or all disadvantages noted in any part of this disclosure.

DETAILED DESCRIPTION

Introduction

Figure 1:
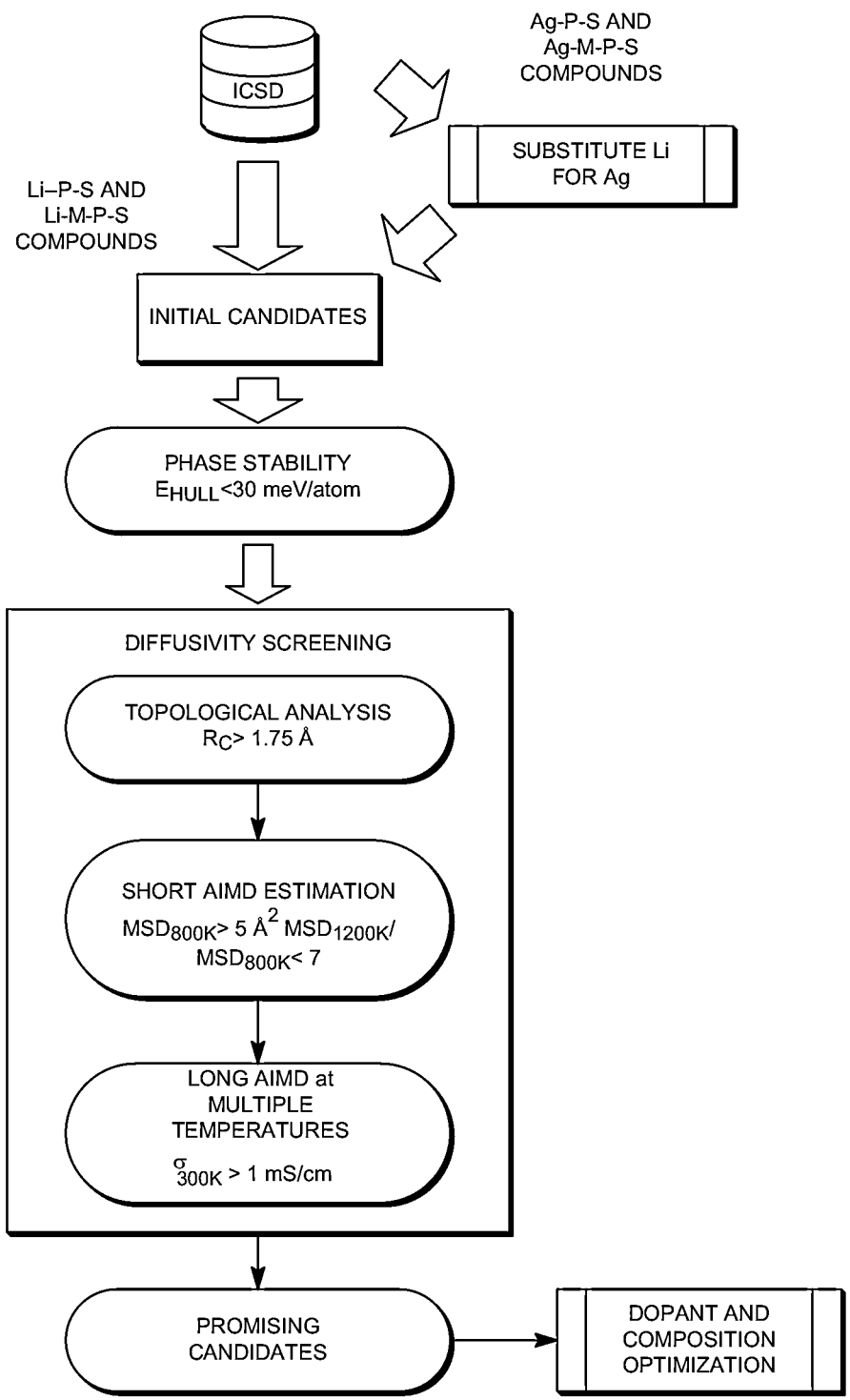
FIG. 1 is a flowchart of the screening procedure for new lithium superionic conductors, where the relative sizes of the arrows indicate the number of candidates remaining after the current screening step.

When surveying the space of known lithium thiophosphates, an interesting observation is that many of them have analogues in Ag thiophosphates. For example, $Li_7P_3S_{11}$ and $Li_3PS_4$ bear remarkable structural similarity to $Ag_7P_3S_1$ and $Ag_3PS_4$ respectively. The highly interesting Li argyrodite superionic conductors with formula $Li_6PS_5X$ (X=Cl, Br, I) derive their name from the mineral argyrodite ($Ag_8GeS_6$), and show promising $Li^+$ conductivities of >1 mS/cm for X=Cl and Br. Many Ag compounds are also known to exhibit extraordinarily high ionic conductivities; for example, $\alpha$-AgI is perhaps the best known, and one of the first superionic conductors ever discovered.

Inspired by this observation, we have performed a comprehensive screening of the ternary Li—P—S and quaternary Li-M-P—S (where M is a non-redox active element) chemical spaces for new lithium superionic conductors using an efficient screening approach based on high-throughput density functional theory (DFT) calculations. The scope of this work extends beyond the known Li thiophosphates and includes new candidates obtained from Ag for Li substitution of Ag thiophosphates. The screening yielded two highly promising candidates, $Li_3Y(PS_4)_2$ and $Li_5PS_4Cl_2$, which are predicted to satisfy the necessary combination of excellent phase and electrochemical stability, high $Li^+$ conductivity, and low electronic conductivity. We also show that the conductivity of the more promising $Li_3Y(PS_4)_2$ material can be further enhanced multi-fold via aliovalent doping. Finally, we will discuss the relative merits of this new superionic conductor compared to current state-of-the-art superionic conductors.

Initial Candidate Selection

The initial pool of candidate lithium superionic conductors was constructed from the following:

1. All known ordered Li—P—S and Li-M-P—S structures from the 2015 version of the In-organic Crystal Structure Database (ICSD). Only non-redox-active elements were allowed for M.
2. Substitution of Ag with Li on all known ordered Ag—P—S and Ag-M-P—S structures from the ICSD.

Unique structures were identified from the pooled candidates using an in-house structure matching algorithm implemented in the Python Materials Genomics (pymatgen) materials analysis library.

DFT Calculations

All DFT calculations were performed using the Vienna Ab initio Simulation Package (VASP) within the projector augmented-wave approach. The exchange-correlation functional and calculation parameters were carefully selected to achieve a balance between computational accuracy and cost for the different types of calculations.

Spin-polarized calculations using the Perdew-Burke-Ernzerhof (PBE) generalized-gradient approximation (GGA) functional was used for all structural relaxations. The convergence parameters, e.g. k-point density of at least 1000/(number of atoms in the unit cell) and energy cutoff of 520 eV, were similar to those used in the Materials Project (MP), which have been tested extensively over a broad range of chemistries.

All structures were fully relaxed using parameters similar to those used in the Materials Project (MP), which has been extensively tested over a broad range of chemistries and materials. All calculations were spin-polarized and performed using the Perdew-Burke-Ernzerhof (PBE) generalized-gradient approximation (GGA) functional. A k-point density of at least 1000/(number of atoms in the unit cell) and an energy cutoff of 520 eV was used. Where available, pre-relaxed structures were first obtained from the MP using the Materials Application Programming Interface (API) to reduce computational cost.

The phase stability of a compound was estimated by determining its energy above the convex hull $E_{hull}$ in the relevant Li—P—S and Li-M-P—S phase diagrams. Stable compounds have an $E_{hull}$ of 0, and the higher the value, the more unstable the compound is at 0 K. Apart from the compounds of primary interest in this work, the energies of existing compounds were extracted from the MP database using the Materials Application Programming Interface (API). To account for overbinding of sulfur in DFT calculations, an energy correction of −0.66 eV per S atom for sulfides was applied.

The phase stability of all compounds of interest were estimated by constructing the relevant Li—P—S and Li-M-P—S phase diagrams using the convex hull construction. The energy above hull $E_{hull}$ is then used as an estimate of thermodynamic stability. Stable compounds have an $E_{hull}$ of 0, and the higher the value, the more unstable the compound is at 0 K. To account for overbinding of sulfur in PBE, an energy correction for sulfides was applied.

The electrochemical stability was assessed using the lithium grand potential phase diagram approach. In this approximation, Li is treated as the main mobile species and the solid electrolyte/electrode interface can be modeled as an open system with respect to Li. The relevant thermodynamic potential is therefore the grand potential, which can be approximated as $\varphi \approx E - \mu_{Li} N_{Li}$ in which E, $N_{Li}$ and $\mu_{Li}$ are DFT total energy, number of lithium atoms in the open system, and lithium chemical potential, respectively. The phase equilibria at the anode and charged cathode can be approximated as the lithium superionic conductor composition at high $\mu_{Li} = \mu°_{Li}$ and low $\mu_{Li} = \mu°_{Li} - 5$ eV ($\mu°_{Li}$ is the chemical potential of metallic Li), respectively.

Automated non-spin-polarized Ab initio molecular dynamics (AIMD) simulations were performed in an NVT ensemble at elevated temperatures with a Nose-Hoover thermostat. A smaller plane-wave energy cutoff of 280 eV, a minimal Γ-centered 1×1×1 k-point mesh, and a time step of 2 fs were adopted. The simulation supercell sizes were at least 9 Å along each lattice direction. In line with previous studies, the simulation cell parameters were fixed at the fully relaxed cell parameters at 0 K. The Li$^+$ diffusivity was obtained via a linear fit of the mean square displacement (MSD) with time, and Arrhenius plots were constructed from simulations at multiple temperatures to obtain the activation energy $E_a$ and extrapolated room-temperature self-diffusivity $D_{300K}$ and conductivity $\sigma_{300K}$.

Climbing image nudged elastic band (CI-NEB) calculations were performed to determine the vacancy migration barriers for the most promising candidates. Overall charge neutrality was achieved via adding a positive background charge. The forces were converged to within 0.05 eV/A.

Regarding the electronic structure band gap calculations were performed using the Heyd-Scuseria-Ernzerhof (HSE) hybrid functional, due to the well-known underestimation of band gaps by semi-local functionals.

Parameterization of Screening Criteria

FIG. 1 is a flowchart showing a schematic of one example of the high-throughput (HT) screening framework described herein, which is tiered based on considerations of the relative importance of each property for lithium solid electrolyte applications and the computational cost required to calculate it.

First and foremost, all technologically relevant materials must be synthesizable, i.e., exhibit good phase stability. In this work, we have adopted a cutoff of $E_{hull} < 30$ meV/atom, which is based on similar cutoffs adopted in previous HT computational materials screening efforts as well as the fact that $Li_7P_3S_{11}$ and $Li_{10}GeP_2S_{12}$, both well-known superionic conductors, have been predicted to have an $E_{hull}$ of 21-25 meV/atom. Of course, depending on circumstances, different cutoffs may be employed as well.

Second, a lithium superionic conductor must have a high Li$^+$ conductivity at room temperature ($\sigma_{300K}$). Due to the near unity transference number of lithium superionic conductors, $\sigma_{300K}$ exceeding 0.1 mS/cm should suffice for comparable performance with organic liquid electrolytes, though $\sigma_{300K} > 1$ mS/cm is preferred. However, obtaining converged diffusivity and conductivity numbers from AIMD simulations is a highly computationally demanding process, usually requiring at least hundreds of picoseconds of simulation time (~50,000-100,000 time steps) at multiple temperatures. Because we are interested only in superionic conductors with extremely high diffusivity, we have adopted a three-step diffusivity screening that includes a topological screening step, a quick estimation step, and a converged screening step.

The topological screening, which is the first step in the screening, is based purely on topological considerations. Only materials exhibiting >1D diffusion networks with a minimum bottleneck size $r_c$ of 1.75 Å, are considered as suitable candidates for lithium superionic conductors. This cutoff is slightly smaller than the channel size for the $Li_{10}GeP_2S_{12}$ superionic conductor (1.84 Å). A looser cutoff is used to avoid screening out too many candidates in the first screening step. The topological evaluation was carried out using the open source software Zeo$^{++}$.

Figure 2:
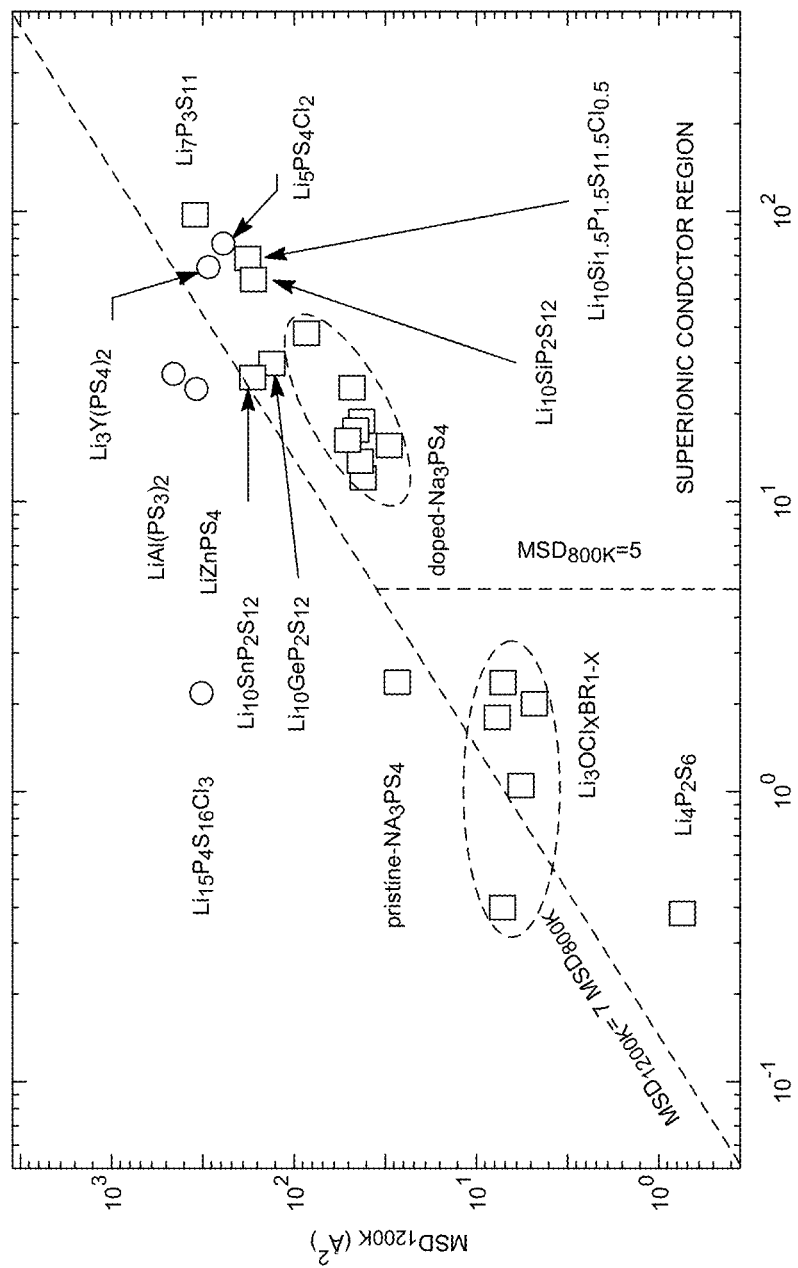
FIG. 2 is a plot of $MSD_{1200K}$ versus $MSD_{800K}$ for a wide range of known alkali conductors and the new candidates described herein.

Regarding the quick estimation step, quick estimates of the diffusivity and activation energy were obtained using the mean square displacements obtained from short AIMD simulations of 50 ps at 800 K ($MSD_{800K}$) and 1200 K ($MSD_{1200K}$). FIG. 2 shows a log-log plot of the $MSD_{1200K}$ versus $MSD_{800K}$ for a wide range of known compounds as well as the materials screened in this work. Square markers indicate known materials, which include well-established superionic conductors as well as relatively poorer conductors. Circle markers indicate new candidates screened.

The known superionic conductors evaluated include an approximate ordered model ($Li_{10}Si_{1.5}P_{1.5}S_{11.5}Cl_{0.5}$, see Supplementary Information for details) for the recently reported $Li_{9.54}Si_{1.74}P_{1.44}S_{11.7}Cl_{0.3}$ superionic conductor, which has the LGPS structure and an extraordinarily high conductivity of 25 mS/cm.

The $Li_{9.54}Si_{1.74}P_{1.44}S_{11.7}Cl_{0.3}$ superionic conductor reported recently has an extraordinarily high ionic conductivity of 25 mS/cm, and has the same framework as the $Li_{10}GeP_2S_{12}$ (LGPS) that reported earlier. To estimate its diffusion characteristics for comparison with our proposed candidates, we first constructed a model based on an approximate composition of $Li_{10}Si_{1.5}P_{1.5}S_{11.5}Cl_{0.5}$. Starting from the conventional cell of LGPS with formula $Li_{20}Ge_2P_4S_{24}$, all Ge were replaced with Si, one P atom was replaced with Si, and one S atom was replaced with Cl, yielding a cell formula of $Li_{20}Si_3P_3S_{23}Cl$, which reduces to $Li_{10}Si_{1.5}P_5S_{11.5}Cl_{0.5}$. An enumeration was performed using the algorithm of Hart et al. was performed to yield all symmetrically distinct orderings of Si/P and S/Cl, and all structures were fully relaxed using DFT calculations employing the same parameters as outlined above. The ordering with the lowest energy structure was then used for subsequent investigations, e.g., AIMD, stability analyses, etc. It should be noted that the experimental structure is a disordered one, but we do not expect the diffusion characteristics to be significantly affected by the choice of the starting structure.

We may observe that all known superionic conductors fall within the white region bounded by $MSD_{800K} > 5$ Å$^2$ and $MSD_{1200K}/MS_{800K} < 7$, and have therefore used these criteria in our screening process. The former criterion ensures a minimum baseline diffusivity, while the second criterion ensures that the activation energy is below ~400 meV.

Non-spin-polarized ab initio molecular dynamics (AIMD) simulations were performed in an NVT ensemble at elevated temperatures with a Nose-Hoover thermostat. A smaller plane-wave energy cutoff of 280 eV, a minimal Γ-centered 1×1×1 k-point mesh, and a time step of 2 fs were adopted. The volume (V) was fixed at the relaxed 0 K volume for AIMD simulations at elevated temperatures, in line with the usual approximations used in previous works. The simulation supercell sizes were at least 9 Å along each lattice direction. All calculations were automated by an in-house automated AIMD workflow.

From the AIMD simulations, the Li self-diffusivity can be obtained via the following expression:

$$D = \frac{\langle [\Delta r(t)] \rangle^2}{2dt} = \frac{MSD}{2dt}, \quad (1)$$

where d is the dimensionality factor that equals 3 for 3D crystal structure, and $\{[\Delta r(t)]\}$ is the average Li$^+$ mean square displacement (MSD) over a time duration t. The self-diffusivity was obtained via a linear fit of the MSD vs 2dt. The Arrhenius plot was constructed from diffusivities at multiple temperatures to obtain the activation energy ($E_a$) and the extrapolated room-temperature self-diffusivity ($D_{300}$).

The room-temperature Li$^+$ conductivity was then estimated via Nernst-Einstein relation:

$$\sigma_{300K} = (\rho z^2 F^2 / RT) \times D_{300K}, \quad (2)$$

where $\rho$, R and F are the molar density of Li$^+$ in the unit cell, gas constant and Faraday's constant, respectively, and T=300 K and z=+1 were used in the expression.

Short AIMD simulations of 60 ps were performed for the quick screening step in order to derive the mean square displacement cutoffs. The first 10 ps (~5,000 time steps) were used for heating up as well as for equilibration, and the trajectories from 10 ps to 60 ps were used to estimate the MSD. Based on our previous AIMD calculations, the diffusivities for most superionic conductors are found on par or beyond the magnitude of $10^{-6}$ cm$^2$/s at 800 K. By combining Eqn. (1) and benchmarking results shown in FIG. 2, we set $MSD_{800K} > 5$ Å$^2$ as the baseline diffusivity criterion.

Assuming that the diffusivity follows an Arrhenius relationship, we can also write the diffusivity as:

$$D = D_0 e^{-\frac{E_a}{kT}}, \quad (3)$$

where $E_a$ is the activation barrier and k is Boltzmann's constant.

Combining Eqn. (1) and (3), we can write:

$$MSD = 2D_0 dt D_0 e^{-\frac{E_a}{RT}} \quad (4)$$

Let us consider the ratio of MSD at 1200 K and 800 K for the same simulation time period t.

$$\frac{MSD_{1200K}}{MSD_{800K}} = e^{-\frac{E_a}{1200k} + \frac{E_a}{800k}}, \quad (5)$$

$$E_a = 2400 \cdot k \, \ln\left(\frac{MSD_{1200K}}{MSD_{800K}}\right). \quad (6)$$

For $\frac{MSD_{1200K}}{MSD_{800K}} < 7$, $E_a < 402$ meV.

The relative trends observed in FIG. 2 are consistent with the known properties of the conductors, with faster conductors such as $Li_{10}Si_{1.5}P_{1.5}S_{11.5}Cl_{0.5}$ exhibiting larger $MSD_{800K}$ (higher diffusivity at 800 K) and lower $MSD_{1200K}/MSD_{800K}$ (lower activation barriers) than slightly poorer conductors such as $Li_{10}GeP_2S_{12}$. It should be noted that though $Li_7P_3S_{11}$ was experimentally reported to have an ionic conductivity of 17 mS/cm, recent computational work by the authors of this work suggests that the intrinsic conductivity of this material may be as high as 60 mS/cm, which accounts for its high $MSD_{800K}$. Also, though $Li_3OCl_xBr_{1-x}$ and $Na_3PS_4$ were initially reported to be superionic conductors, the pristine crystalline phases have been shown to have low room-temperature conductivities, and higher ionic conductivities are obtained only with the introduction of a large number of defects/dopants (e.g., doped-$Na_3PS_4$) and/or via amorphization.

Finally, in the converged screening step, longer AIMD simulations at six temperatures were performed on the materials that pass the first two screening steps to obtain converged diffusivities (and conductivities) and activation barriers.

The above three-step screening process allows us to rapidly eliminate poor candidates with a minimum amount of computational resources, and devote expensive AIMD simulations to obtain converged diffusivity statistics on the most promising materials.

Besides excellent Li$^+$ conductivity, a solid electrolyte for all-solid-state rechargeable
lithium-ion batteries must also be electronically insulating and exhibit good electrochemical stability against the electrodes. An assessment of these properties were carried out for the most promising candidates.
Identification of Potential Candidates Table 1 summarizes the phase stability, topological parameters and rapid AIMD screening results of all new Li—P—S and Li-M-P—S candidates. The rapid AIMD screening results are also presented in FIG. 2 for comparison with known superionic conductors. We note that though we did perform Ag for Li substitution of Ag—P—S compounds, the derived compounds are all well-known compounds such as $Li_7P_3S_{11}$ and $Li_3PS_4$ that have already been extensively explored as lithium superionic conductors, and thus will not be considered further here.

TABLE 1

| Compound | Source (ICSD number) | $E_{hull}$ (meV/atom) | $r_c$ (Å) | $MSD_{800K}$ (Å$^2$) | $MSD_{800K}$/$MSD_{800K}$ |
|---|---|---|---|---|---|
| Promising candidates | | | | | |
| $Li_3Y(PS_4)_2$ (C2/c) | $Ag_3Y(PS_4)_2$ (417658) | 2 | 1.88 | 65.1 | 4.5 |
| $Li_3PS_4Cl_2$ (C2mm) | $Ag_3PS_4Cl_2$ (416587) | 17 | 1.76 | 77.9 | 3.1 |

TABLE 1-continued

| Compound | Source (ICSD number) | $E_{hull}$ (meV/atom) | $r_c$ (Å) | $MSD_{800K}$ (Å$^2$) | $MSD_{800K}$ / $MSD_{800K}$ |
|---|---|---|---|---|---|
| Candidates failing at least one screening criteria | | | | | |
| $Li_{15}P_4S_{16}Cl_3$ ($I\bar{4}3d$) | $Ag_{18}P_4S_{16}Cl_3$ (416586) | 8 | 1.76 | 2.2 | 145.1 |
| $LiZnPS_4$ ($I\bar{4}$) | ICSD (95785) | 0 | 1.83 | 24.7 | 13.9 |
| $LiAl(PS_3)_2$ (C2/c) | ICSD (425979) | 0 | 1.82 | 27.8 | 16.5 |
| $Li_2Zn(PS_3)_2$ (C2/c) | $Ag_2Zn(PS_3)_2$ (72719) | 33 | 1.84 | — | — |
| $LiIn(PS_3)_2$ ($P\bar{3}1c$) | $AgIn(PS_3)_2$ (202185) | 0 | 0 | — | — |
| $LiZnPS_4$ ($Pna2_1$) | $AgZnPS_4$ (48197) | 16 | 0 | — | — |

Among the new quaternary compounds, only $Li_3Y(PS_4)_2$ (LYPS) and $Li_5PS_4Cl_2$ (LP-SCl) satisfy all the initial screening criteria: low $E_{hull}$, $r_c$>1.75 Å, $MSD_{800K}$>5 Å$^2$ and $MSD_{1200K}/MSD_{800K}$<7. Their $MSD_{800K}$ are on par with that of the leading LGPS-based candidate, $Li_{10}Si_{1.5}P_{1.5}S_{11.5}Cl_{0.5}$, but their $MSD_{1200K}/MSD_{800K}$ ratios are slightly higher. Though $Li_{15}P_4S_{16}Cl_3$, $LiZnPS_4$ and $LiAl(PS_3)_2$ are also predicted to have fairly low $E_{hull}$ and reasonably high $MSD_{800K}$, their $MSD_{200K}/MSD_{800K}$ are far too high, indicating high activation barriers. The remaining candidates do not pass either the phase stability criterion or the topological screening. During the preparation of this manuscript, it has come to our attention that the $LiZnPS_4$ candidate in Table 1 has been investigated as a superionic conductor. Our screening calculations show that the stoichiometric $LiZnPS_4$ compound fails the MSD ratio cutoff by a factor of 2, which is consistent with the high activation barriers reported for the stoichiometric compound reported in Richards et al.'s work. A more in-depth comparison of our proposed candidates with known superionic conductors is provided below.

Figure 3A:
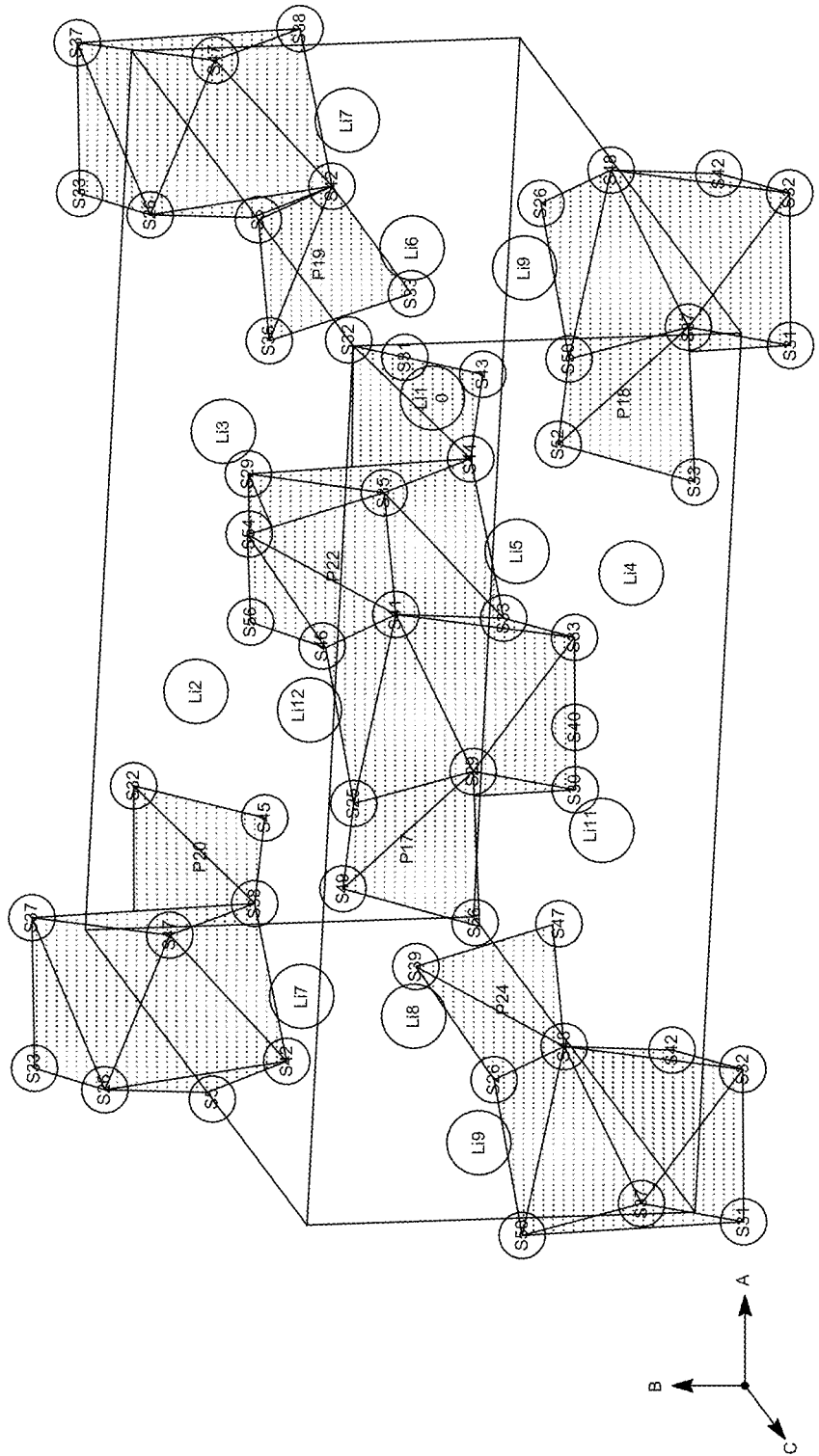
FIG. 3a shows the crystal structure (conventional cell) of $Li_3Y(PS_4)_2$ and FIG. 3b shows the crystal structure (conventional cell) of $Li_5PS_4Cl_2$.
Figure 3B:
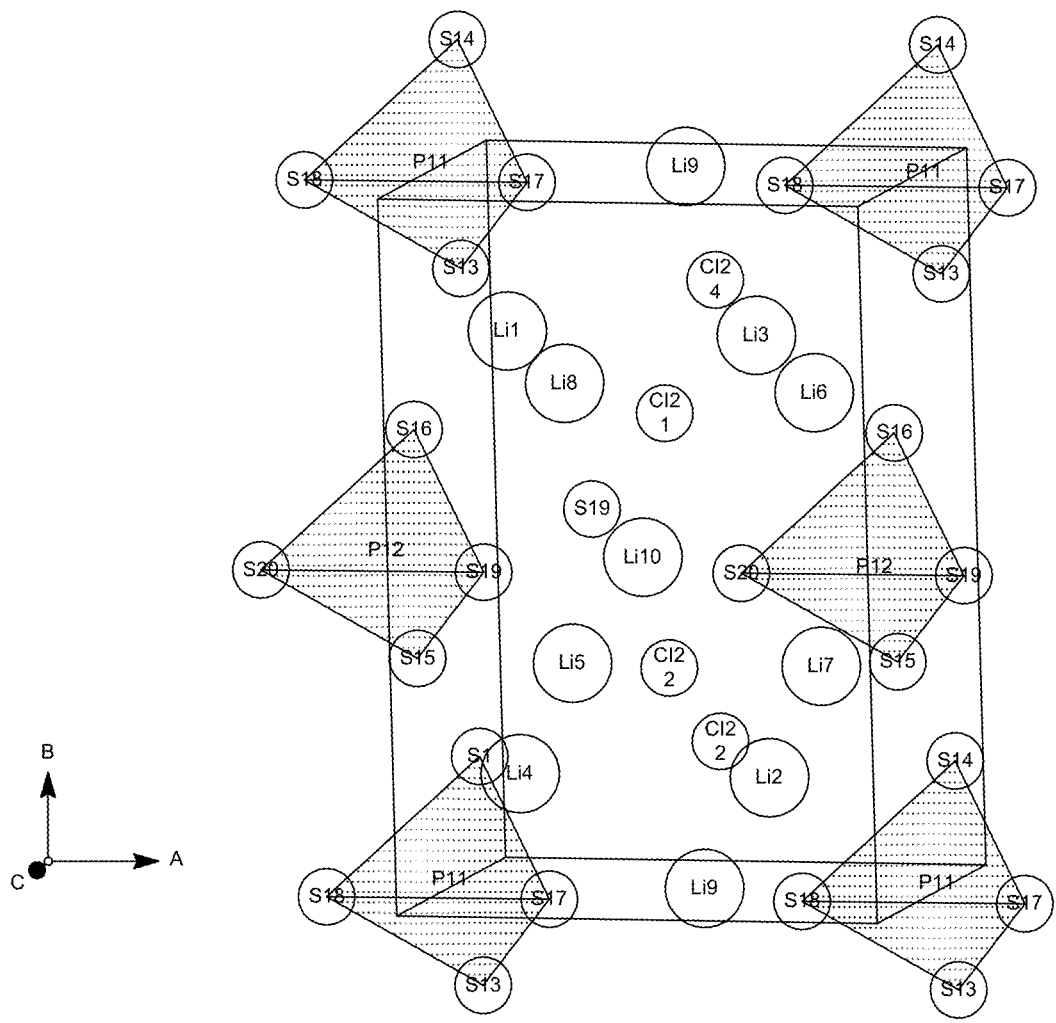

The crystal structures of LYPS and LPSCl are shown in FIG. 3, and the relaxed lattice parameters are given in Table 2. LYPS and LPSCl belong to the monoclinic C2/c and orthorhombic C2 mm space groups, respectively. Both LYPS and LPSCl structures have two symmetrically distinct Li sites, which are labeled as Li1 and Li2 in FIGS. 6 and 7.

TABLE 2

| Compound | atoms/cell | a (Å) | b (Å) | c (Å) | α (°) | β (°) | γ (°) |
|---|---|---|---|---|---|---|---|
| $Li_3Y(PS_4)_2$ | 56 | 17.122 | 9.290 | 9.137 | 90.0 | 122.3 | 90.0 |
| $Li_5PS_4Cl_2$ | 24 | 7.212 | 10.494 | 6.024 | 90.0 | 90.0 | 90.0 |

Li$^+$ Conductivities and Mechanisms

Figure 4:
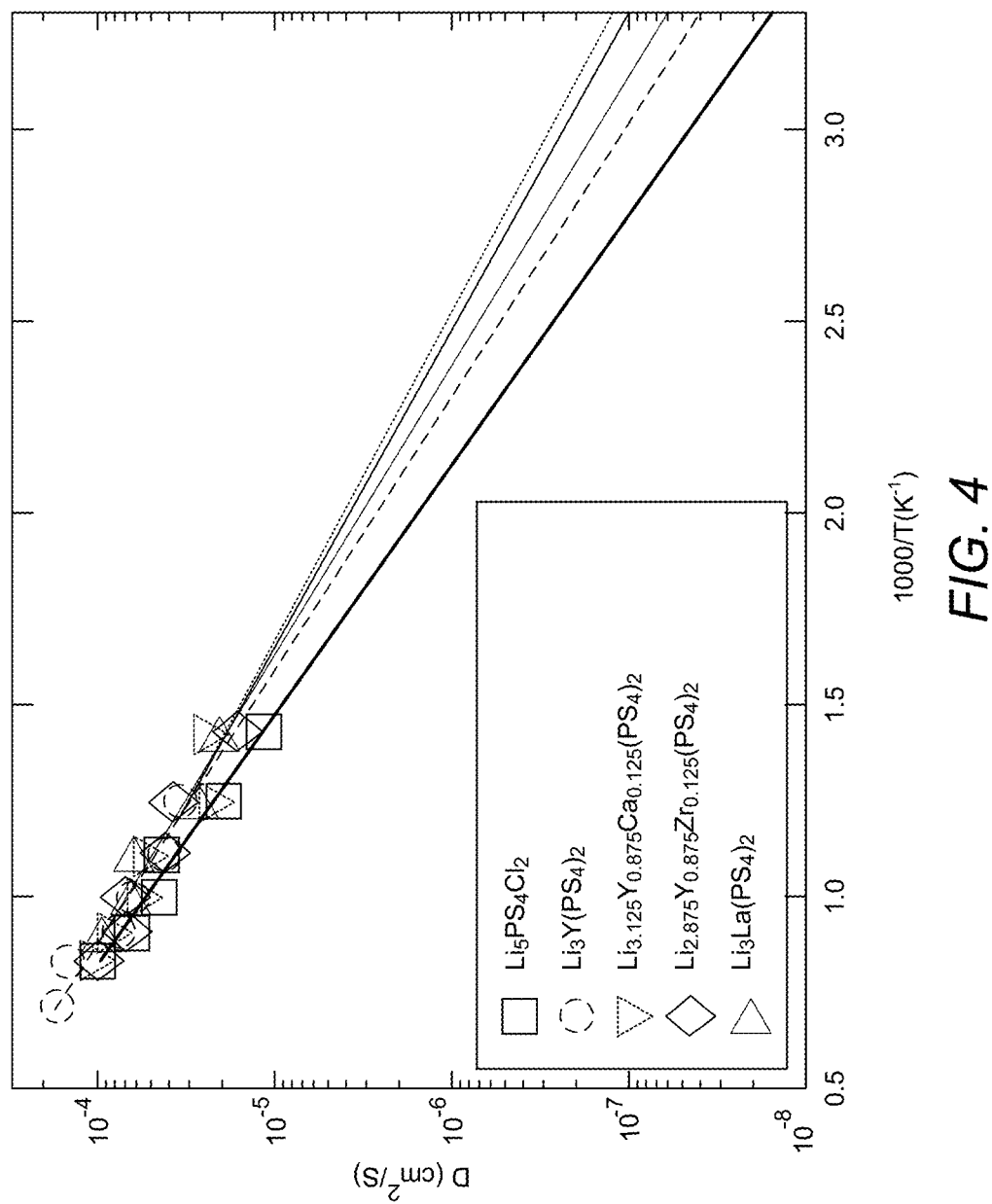
FIG. 4 shows Arrhenius plots of promising lithium superionic conductor candidates from AIMD simulations, where solid lines indicate the initial $Li_3Y(PS_4)_2$ and $Li_5PS_4C_{12}$ candidates and dashed lines indicate the further optimized candidates obtained via aliovalent doping or substitution of $Li_3Y(PS_4)_2$, $(Li_3La(PS_4)_2$, $Li_{3.125}Y_{0.875}Ca_{0.125}(PS_4)_2$ and $Li_{2.875}Y_{0.875}ZrO_{0.125}(PS_4)_2)$.

Long AIMD simulations of at least 200 ps at multiple temperatures were performed on the promising LYPS and LPSCl candidates. FIG. 4 shows the Arrhenius plot of the diffusivity versus 1000/temperature for the two candidates, and Table 3 summarizes the key conductivity properties extracted. In FIG. 4, dashed lines indicate the further optimized candidates obtained via aliovalent doping or substitution of $Li_3Y(PS_4)_2$ ($Li_3La(PS_4)_2$, $Li_{3.125}Y_{0.875}Ca_{0.125}(PS_4)_2$ and $Li_{2.875}Y_{0.875}Zr_{0.125}(PS_4)_2$).

TABLE 3

| Formula | $\sigma_{300K}$ (mS/cm) | Error range of $\sigma_{300K}$ (mS/cm) | $E_a$ (meV) | $D_{300K}$ (cm$^2$/s) |
|---|---|---|---|---|
| $Li_3Y(PS_4)_2$ | 2.16 | [1.46, 3.19] | 278 | 3.56 × 10$^{-8}$ |
| $Li_5PS_4Cl_2$ | 1.85 | [1.38, 2.47] | 304 | 1.36 × 10$^{-8}$ |

The estimated activation energies $E_a$ for LYPS and LPSCl are 278 meV and 304 meV, respectively. The extrapolated room-temperature conductivities are 2.16 mS/cm for LYPS and 1.85 mS/cm for LPSCl, i.e., both candidates are indeed verified to be lithium superionic conductors.

Figure 5A:
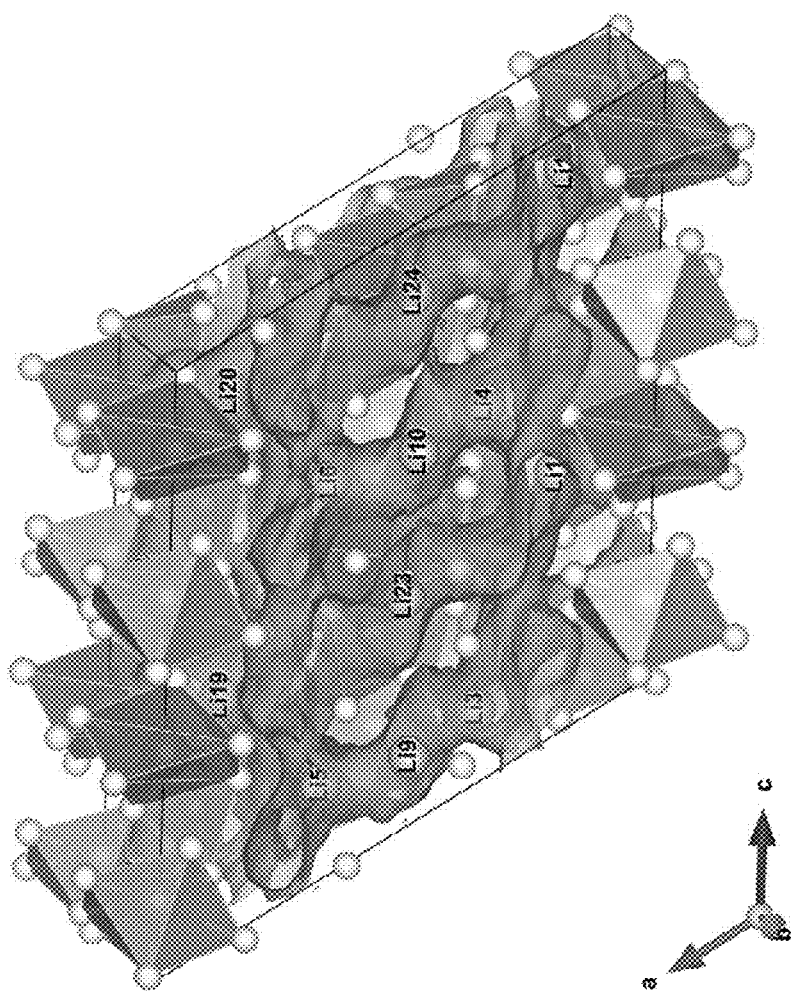
FIG. 5A and FIG. 5B are isosurfaces of $Li^+$ probability density distribution P for $Li_3Y(PS_4)_2$ and $Li_5PS_4Cl_2$ from AIMD simulations at 800 k with $P=0.0001\ a_0^{-3}$ ($a_0$ is the Bohr radius).
Figure 5B:
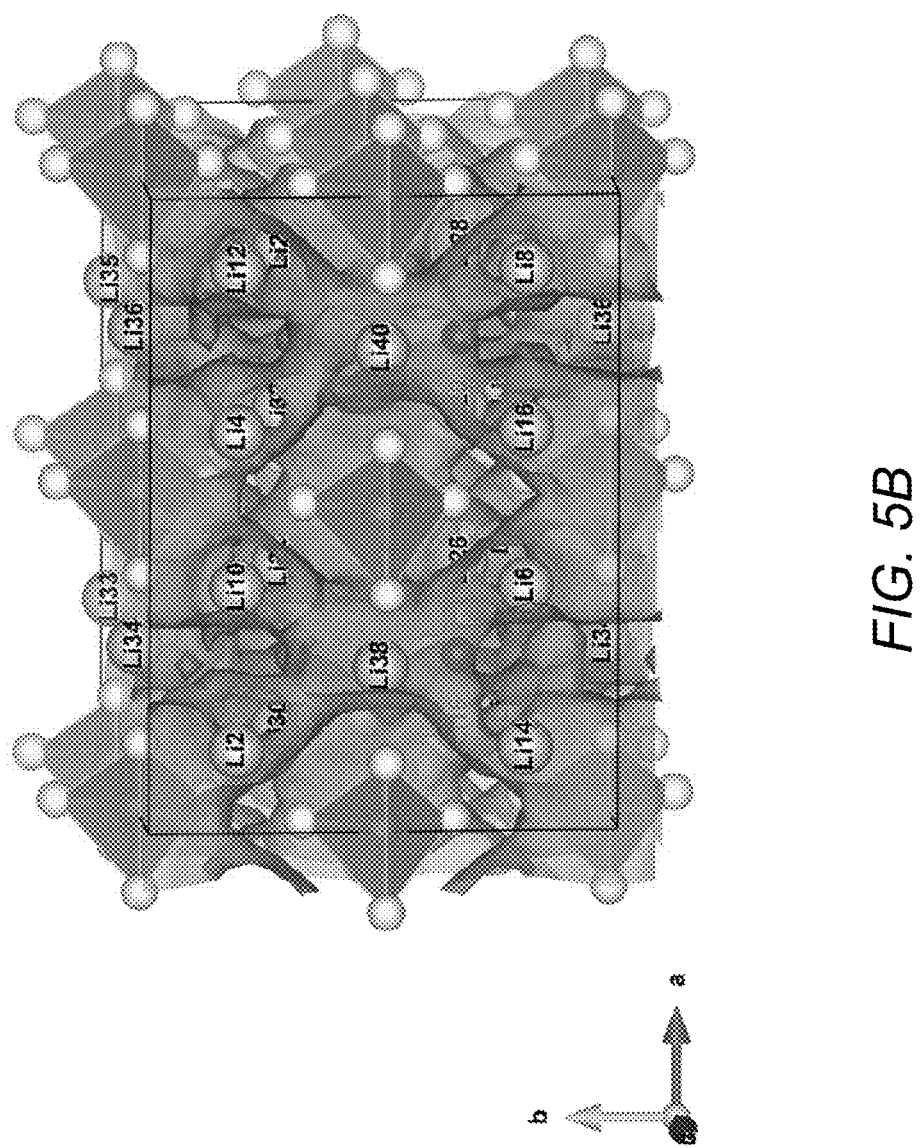
Figure 6A:
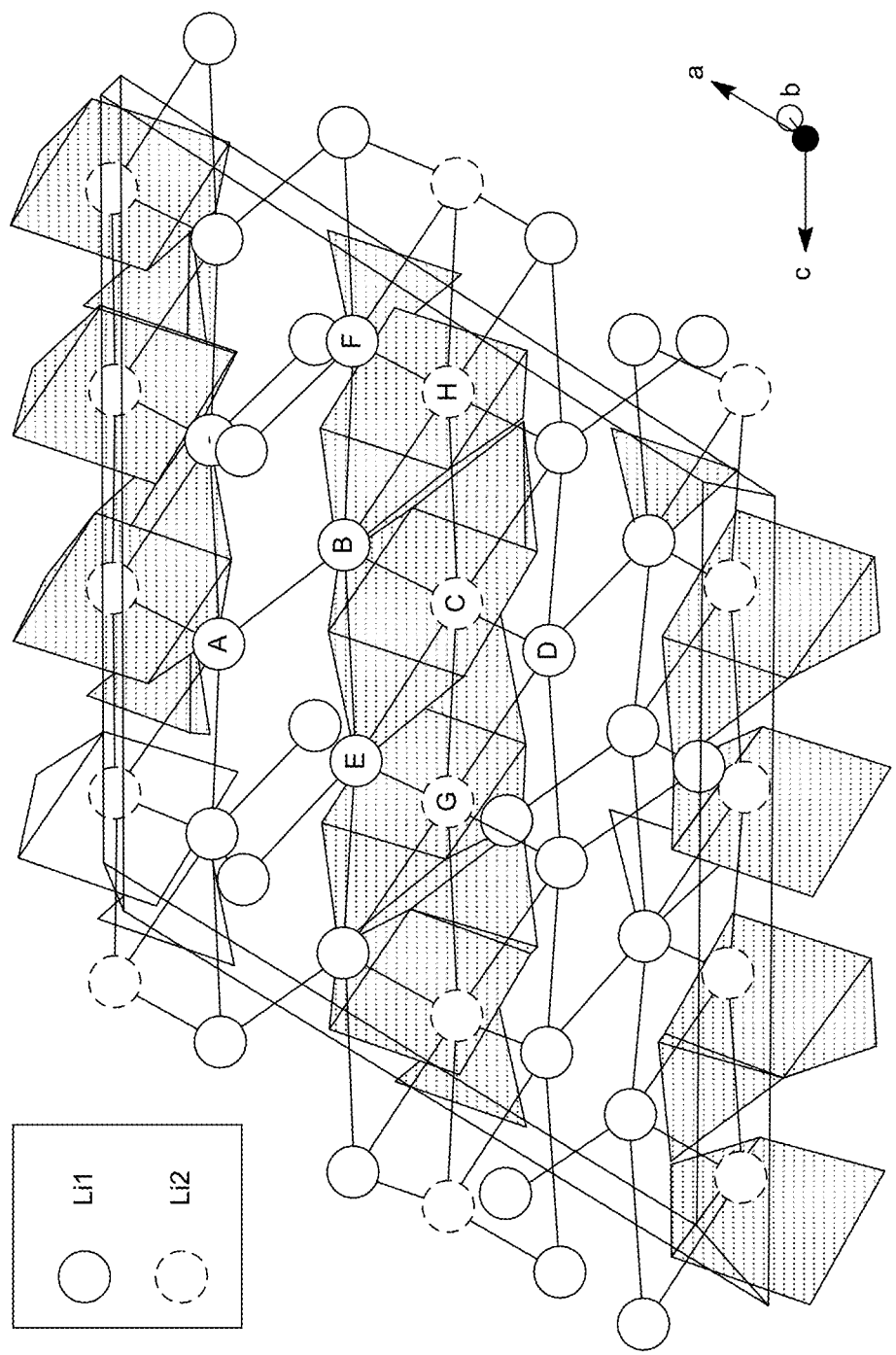
FIG. 6(a) shows the investigated Li vacancy diffusion paths in $Li_3Y(PS_4)_2$ viewed along the b direction and FIGS. 6(b)-6(d) show the calculated CI-NEB migration barriers for selected percolating paths.
Figure 6B:
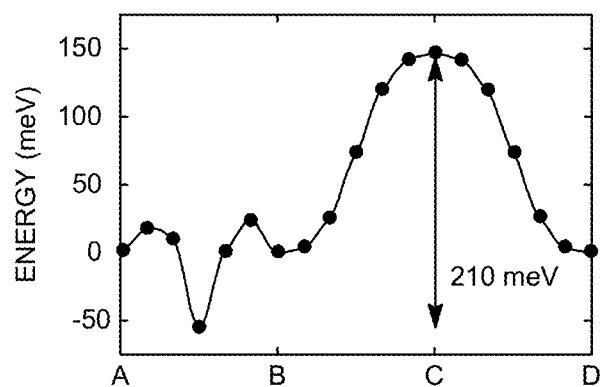
Figure 6C:
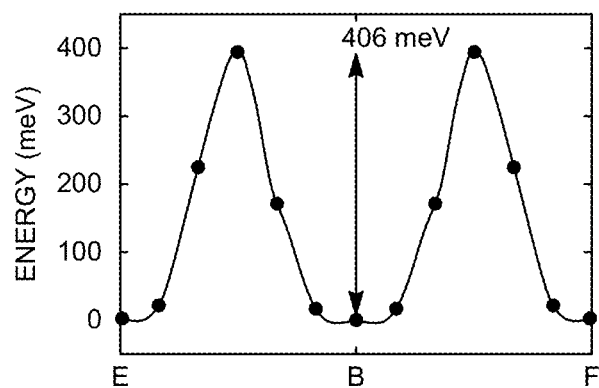
Figure 6D:
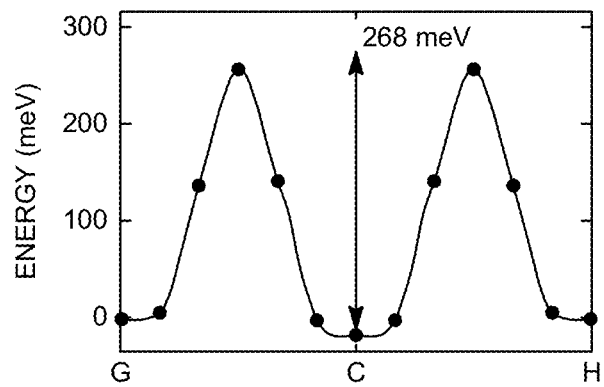
Figure 7A:
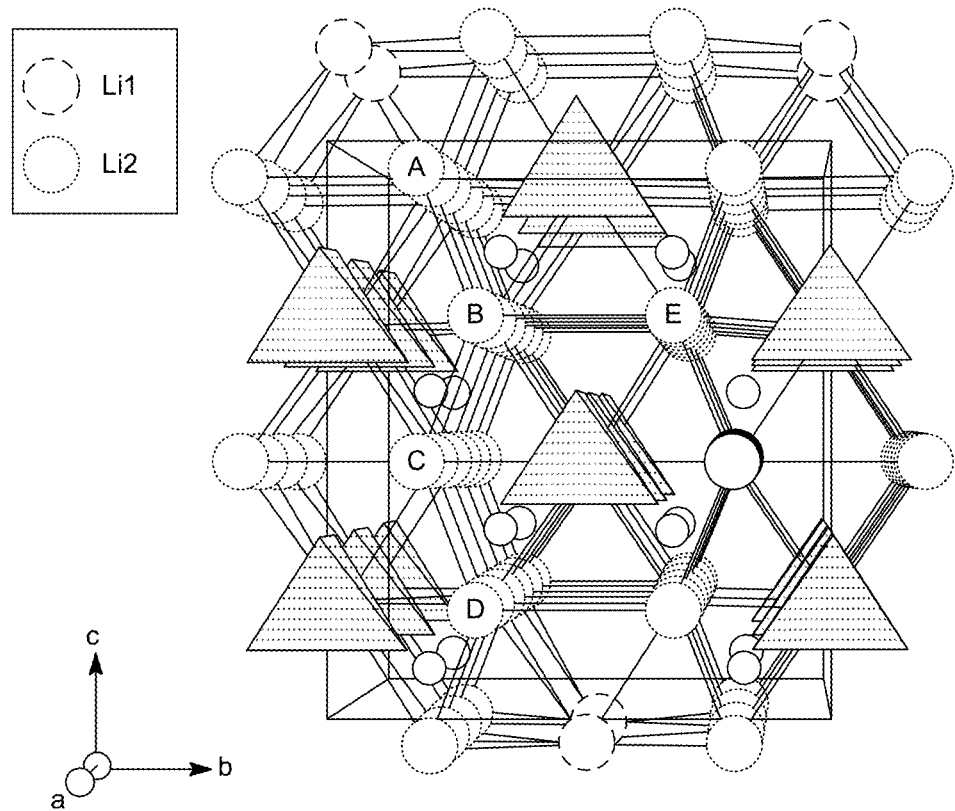
FIG. 7a shows the investigated Li vacancy diffusion paths in $Li_5PS_4Cl_2$ viewed along the a direction and FIG. 7b shows the investigated Li vacancy diffusion paths along the b direction and FIGS. 7(c)-7(e) show calculated CI-NEB migration barriers for selected paths.
Figure 7B:
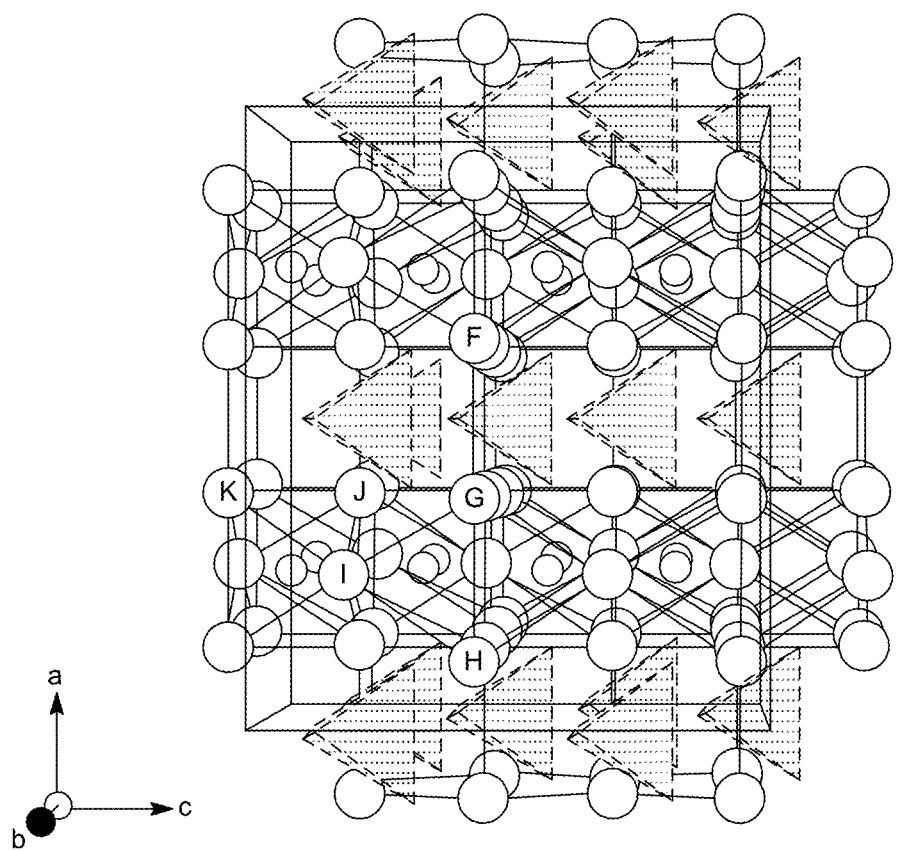
Figure 7C:
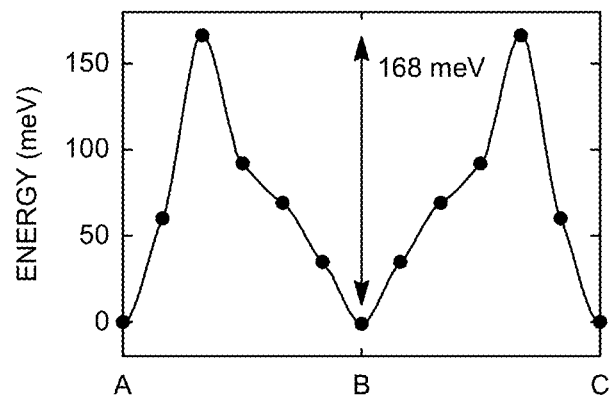
Figure 7D:
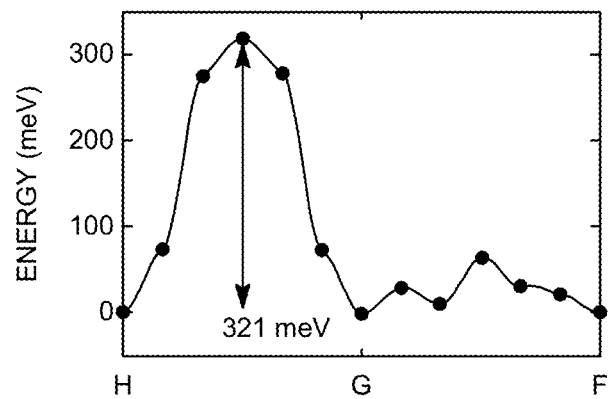
Figure 7E:
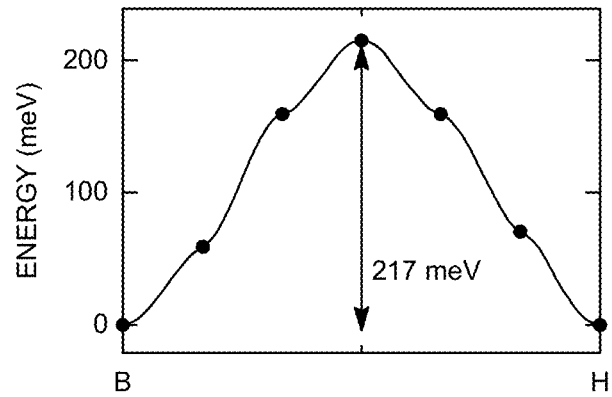

To further understand the atomistic diffusion mechanisms and pathways, the Li probability density function (PDF) was calculated from the AIMD simulations of the two candidates at 800 K, and CI-NEB calculations were performed to calculate the vacancy migration barriers in the identified pathways. FIGS. 5A and 5B shows isosurfaces of Li$^+$ probability density distribution P (light blue) for $Li_3Y(PS_4)_2$ and $Li_5PS_4Cl_2$ from AIMD simulations at 800 K with P=0.0001 $a_0^{-3}$ ($a_0$ is the Bohr radius). From FIGS. 5A and 5B, we observe that both candidates have 3D diffusion networks. Schematics of the identified diffusion pathways and the corresponding calculated CI-NEB migration barriers are given in FIGS. 6 and 7 for LYPS and LPSCl, respectively. FIG. 6(a) shows the investigated Li vacancy diffusion paths in $Li_3Y(PS_4)_2$ viewed along b direction. FIGS. 6(b)-6(d) show the calculated CI-NEB migration barriers for selected percolating paths. FIG. 7 shows the investigated Li vacancy diffusion paths in $Li_5PS_4Cl_2$ viewed along the a direction (FIG. 7a), the b direction (FIG. 7b). FIGS. 7(c)-7(e) show calculated CI-NEB migration barriers for selected paths.

For LYPS, there are five symmetrically distinct hops between neighboring Li sites, namely, A→B, B→F, B→C, C→E and C→H (see FIG. 6). We may observe that the lowest barrier percolating pathway in LYPS is A→B→C→D (all Li1) with a barrier of 210 meV. To enable >1D diffusion, the next lowest barrier pathway is G→C→H (all Li2) along the c direction with an overall barrier of 268 meV. The E→B→F pathway has a much higher overall barrier of 406 meV, which suggests it is more likely for a vacancy at E to diffuse to B via the lower barrier E→G→C→B path. The estimated effective 3D vacancy migration barrier (268 meV) is therefore in good agreement with the activation energy from AIMD simulations (278 meV).

For LPSCl, we may observe that the crystal structure comprises layers of Li1 and Li2 (see FIG. 7) in the b-c plane stacked along the a direction. Within each Li1 plane, the vacancy migration barriers are relatively low (A→B→C→D with overall barrier of 166 meV, and B→E with barrier of 217 meV). For 3D diffusion, the H→G→F Li1-only path connecting different Li1 layers has the lowest overall barrier of 321 meV. This is again in reasonably good agreement with the AIMD activation energy of 304 meV. All other paths involving vacancy hops between Li1 and Li2 sites have significantly higher barriers (>380 meV).

Electronic Band Gap

Figure 8A:
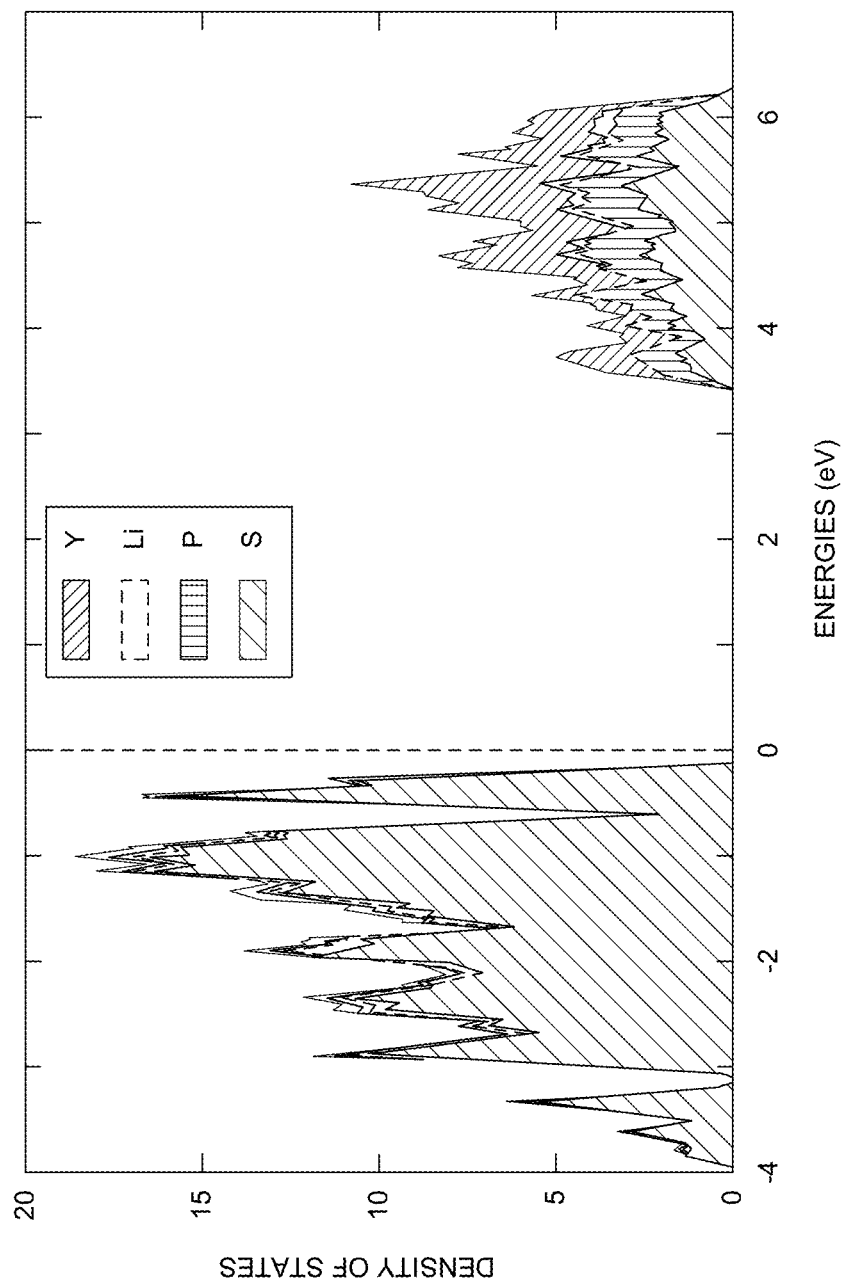
FIG. 8a shows the calculated element-projected density of states for $Li_3Y(PS_4)_2$ (band gap Eg=3.41 eV)
Figure 8B:
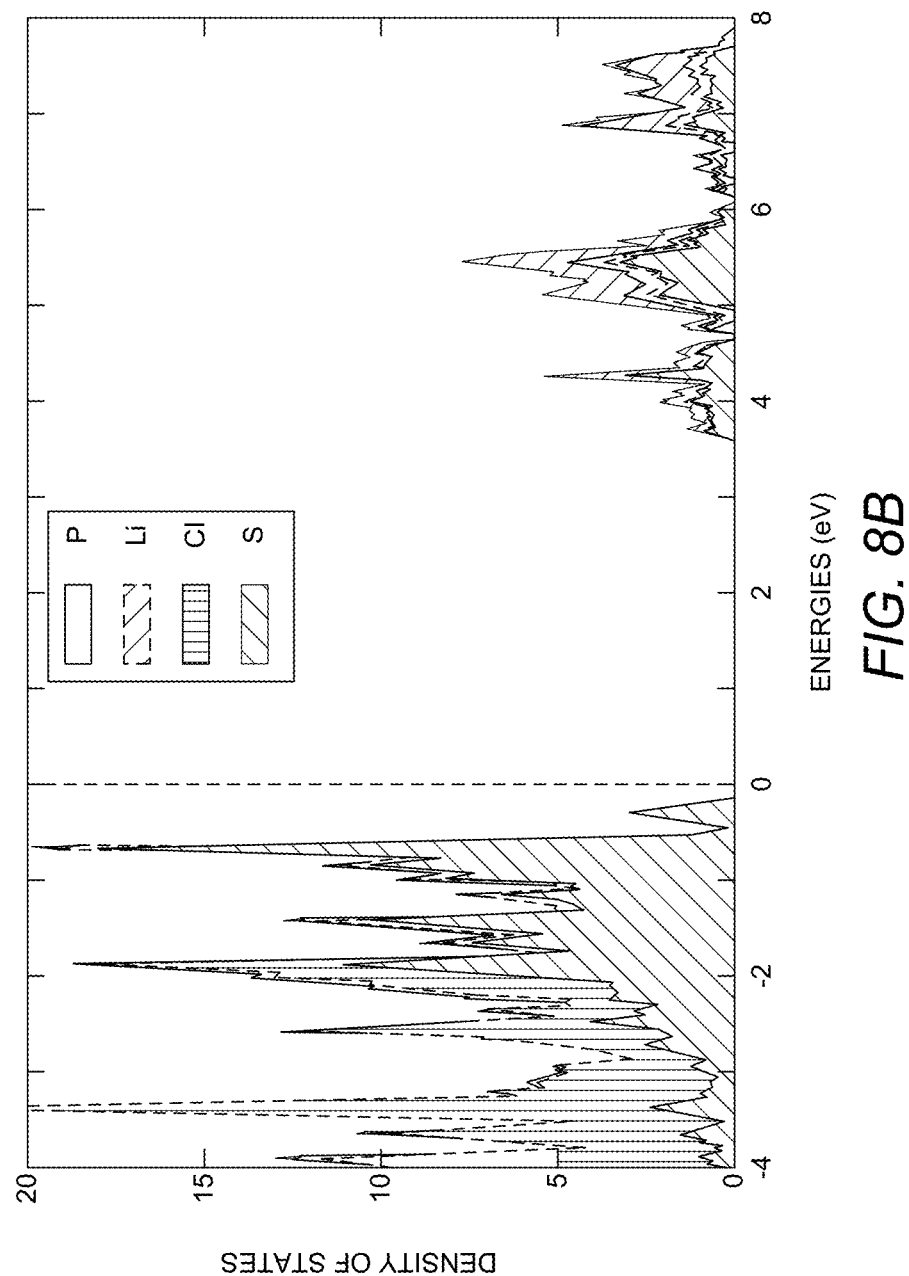
FIG. 8(b) shows the calculated element-projected density of states for $Li_5PS_4Cl_2$ (Eg=3.57 eV) using the HSE screened hybrid functional.

FIG. 8 shows the calculated HSE densities of states for LYPS and LPSCl. FIG. 8(a) shows the density of states for $Li_3Y(PS_4)_2$ (band gap $E_g$=3.41 eV) and FIG. 8(b) shows the density of states for $Li_5PS_4Cl_2$ ($E_g$=3.57 eV) using the HSE screened hybrid functional. Both candidates are large band gap (>3 eV) insulators. In both candidates, the valence band maximum is dominated by anion S-p character, whereas the conduction band minimum has contributions from the framework cations (Y and P) as well as anion S.

The band gap is also an upper limit for the intrinsic stability of the material against
reduction (acceptance of an electron) and oxidation (loss of an electron). Similar to other sulfide-based solid-electrolytes, the intrinsic electrochemical stability of the two candidates are limited to ~3.5 eV.

Electrochemical Stability

Better estimates of the electrochemical stabilities of LYPS and LPSCl were obtained using the lithium grand potential approach. Table 4 summarizes the predicted phase equilibria at the solid electrolyte/anode (metallic Li) interface and solid electrolyte/charged 5V cathode interface. The dominant product at the anode is $Li_2S$ in all cases, which is a good electronic insulator and reasonable Li conductor, especially as an amorphous interphase. The other products at the anode are YP, a semiconductor with band gap of ~1 eV,[55] and $Li_3P$. On the solid electrolyte/charged cathode, $P_2S_5$ is always predicted to be one of the products. However, the presence of $S_2Cl_2$ and $PCl_5$ at the LPSCl/cathode interface may prove problematic in real-world applications as they undergo hydrolysis readily to form HCl.

$E_{hull}$) and excellent topological characteristics (>1 D large conduction channels), and are predicted to be electronic insulators with high $Li^+$ conductivities (exceeding 1 mS/cm). The $Li^+$ conduction mechanisms and migration barriers were elucidated using CI-NEB calculations, and the results further confirm the predictions from the AIMD simulations. In addition, both candidates comprise entirely of earth-abundant elements, making them practical from a cost perspective.

Both candidates are derived from the replacement of Ag with Li in known quaternary Ag thiophosphates in the ICSD. We see this as a further positive attribute of the two candidates as ion exchange from the known Ag-based compounds is therefore a potential initial synthesis route that can be explored. For example, ion exchange has similarly been used to synthesize the well-known $Li_7P_3S_{11}$ superionic conductor from $Ag_7P_3S_{11}$. We speculate that due to the significantly larger ionic radii of Ag (129 pm) compared to Li (90 pm), Li-substituted Ag compounds may present large percolating voids conducive to fast 3D Li mobility. Such a strategy can certainly be expanded beyond just the thiophosphate chemistries that are the focus of this work. However, we would point out that the large ionic radii difference between Ag and Li can potentially lead to incompatibility of Li with the Ag-based host framework, which is why a computational assessment of phase stability is a critical first step to determine the likelihood of synthesis. Also, not all Ag compounds have percolating 3D diffusion networks of sufficient channel size. Here again, the efficient tiered screening approach outlined in this work based on inexpensive topo-

TABLE 4

| Electrolyte | Phase equilibria at 5 V cathode $\mu Li = \mu°Li$ eV | Phase equilibria at anode $\mu Li = (\mu°Li - 5)$ eV |
|---|---|---|
| | Promising candidates | |
| $Li_3Y(PS_4)_2$ | $YPS_4 + 0.5 P_2S_5 + 1.5S$ | $YP + Li_3P + 8 Li_2S$ |
| $Li_5PS_4Cl_2$ | $0.067 PCl_5 + 0.833 S_2Cl_2 + 0.467 P_2S_5$ | $Li_3P + 4 Li_2S + 2 LiCl$ |
| | Known superionic conductors | |
| $Li_{10}Si_{1.5}P_{1.5}S_{11.5}Cl_{0.5}$ | $0.75 P_2S_7 + 0.25 S_2Cl_2 +$ | $1.5 Li_3P + 0.3 Li_{21}Si_5 + 0.5$ |
| $Li_{10}GeP_2S_{12}$ | $1.5 SiS_2 + 2.75 S$ | $LiCl + 11.5 Li_2S\ 2\ Li_3P + 0.25$ |
| $Li_7P_3S_{11}$ | $P_2S_5 + GeS_2 + 5 S$ | $Li_{15}Ge_4 + 12 Li_2S_3\ Li_3P + 11$ |
| | $1.5 P_2S_5 + 3.5 S$ | $Li_2S$ |

For comparison, Table 4 also presents the predicted phase equilibria for the $Li_{10}Si_{1.5}P_{1.5}S_{11.5}Cl_{0.5}$ model of the recently reported $Li_{9.54}Si_{1.74}P_{1.44}S_{11.7}Cl_{0.3}$ superionic conductor as well as $Li_{10}GeP_2S_{12}$ and $Li_7P_3S_{11}$. Similar to the candidates identified in this work, $Li_2S$ is predicted to be the dominant product at the anode/electrolyte interface in all instances, with the small band gap $Li_3P$ comprising a relatively small fraction. For $Li_{10}Si_{1.5}P_{1.5}Cl_{0.5}$ and $Li_{10}GeP_2S_{12}$, there is an additional $Li_{21}Si$, or $Li_{15}Ge_4$ phase, which also have a small band gap, consistent with previous experimental studies. At the cathode/$Li_{10}Si_{1.5}P_{1.5}S_{11.5}Cl_{0.5}$ interface, $S_2Cl_2$ is predicted to be one of the products, though the proportion is much less in comparison to LPSCl due to the much lower content of Cl.

Analysis

From the results in the preceding sections, $Li_3Y(PS_4)_2$ (LYPS) and $Li_5PS_4Cl_2$ (LPSCl) have emerged as promising new lithium superionic conductors based on a comprehensive screening of the Li—P—S and Li-M-P—S chemical spaces. Both candidates exhibit good phase stability (low logical analysis followed by more computationally intensive first principles calculations can provide useful guidelines.

Between the two candidates, LYPS is believed to be the more promising one. Not only is LYPS predicted to have a marginally higher $Li^+$ conductivity than LPSCl in AIMD
simulations, it is also predicted to be significantly more stable ($E_{hull}$=2 meV/atom) and its lack of Cl means that there is likely to be fewer issues with reaction products at higher voltages. We will note that like all sulfide-based materials, air and moisture stability may be a potential area of concern, though this limitation has not prevented the development of prototype all-solid-state rechargeable lithium-ion batteries utilizing other sulfide solid electrolytes. Like other sulfides, both materials are predicted to be relatively soft, which should make it easier to achieve low porosity using cold-pressing methods.

Further Optimization of LYPS

To explore if further enhancement of the conductivity of LYPS is possible, we performed isolvalent substitutions and aliovalent doping of LYPS. $La^{3+}$ was examined as a potential substitute for $Y^{3+}$ due to its slightly larger ionic radii (117 pm compared to 104 pm for $Y^{3+}$). The computed $E_{hull}$ for $Li_3La(PS_4)_2$ is 20 meV, significantly higher than LYPS, and its ionic conductivity is only slightly higher at 3.27 mS/cm with a slightly lower activation energy of 263 meV (see FIG. 4), which can be attributed to the ~ 5% volume expansion and increase in channel size (1.92 Å).

Unlike isovalent substitutions, aliovalent doping can have the additional effect of introducing $Li^+$ vacancies or interstitials. Both $Ca^{2+}$ or $Zr^{4+}$ dopants that have comparable ionic radii to $Y^{3+}$ were explored using a 1×1×2 supercell of LYPS, with the introduction of $Li^+$ interstitials and vacancies, respectively. Table 5 summarizes the dopant formation energies and room-temperature $Li^+$ conductivities for the doped structures. Both $Ca^{2+}$ and $Zr^{4+}$ were found to have reasonably low dopant formation energies of 0.63 eV and 0.26 eV, respectively. From AIMD simulations, we find that aliovalent doping of LYPS with the introduction of either vacancies or interstitials can lead to multi-fold increases in its ionic conductivity. Substitution of 12.5% of $Y^{3+}$ with $Ca^{2+}$ and $Zr^{4+}$ leads to extrapolated room temperature conductivities of 7.14 mS/cm and 5.25 mS/cm, respectively, with corresponding decreases in activation energies to 231 meV and 241 meV, respectively (see FIG. 4).

$Li_{10}GeP_2S_{12}$ (25 meV/atom) and $Li_{10}Si_{1.5}P_{1.5}S_{11.5}Cl_{0.5}$ (30 meV/atom). Recently, computational evidence has been reported of extraordinarily high $Li^+$ conductivities exceeding 50 mS/cm in the $Li_{1+2x}Zn_{1-x}PS_4$ solid solution, a compound that was also considered in our screening. However, these high conductivities were obtained only with the introduction of a large number of defects, requiring high predicted synthesis temperatures exceeding 950 K. In comparison, doped LYPS with conductivities of up to 7 mS/cm still maintains a relatively low $E_{hull}$ and small dopant formation energies.

In terms of interfacial stability, there are no reaction products of major concern at the cathode/LYPS interface, unlike $Li_{10}Si_{1.5}P_{1.5}S_{115}Cl_{0.5}$ where the presence of Cl is predicted to result in the formation of $S_2Cl_2$. On the anode/LYPS interface, the presence of the semiconducting YP phase may be of potential concern, though its band gap (~1 eV) is still higher than the Li—Si alloys (e.g., band gaps of 0.6 eV for $Li_{12}Si_7$ and 0.08 eV for $Li_7Si_3$) predicted to form at the anode/$Li_{10}Si_{15}P_{15}S_{11.5}Cl_{0.5}$ interface. An electrically insulating interface is desired for passivation to avoid further propagation of the reaction front. Furthermore, Li—Si alloys are also well known to undergo significant volume expan-

TABLE 5

| Dopant | Formula | $E_f$ (eV) | $E_{hull}$ (meV/atom) | $\sigma_{300K}$ (mS/cm) | error range of ($\tilde{mS}$/cm) | $E_a$ (meV) |
|---|---|---|---|---|---|---|
| Ca | $Li_{3.125}Y_{0.875}Ca_{0.125}(PS_4)_2$ | 0.63 | 6 | 7.14 | [4.67, 10.92] | 231 |
| Zr | $Li_{2.875}Y_{0.875}Zr_{0.125}(PS_4)_2$ | 0.26 | 4 | 5.25 | [3.77, 7.31] | 241 |

Due to computational cost considerations, our explorations of dopant optimization is limited by the size of the supercell accessible within AIMD simulations. Nevertheless, the doping results are a proof of concept that there is significant scope for further fine-tuning of dopant and Li concentration in LYPS to achieve even higher conductivities, a claim that we hope will be verified by experimental efforts at synthesizing undoped and doped LYPS.

Comparison with Other State-of-the-Art Superionic Conductors

In comparison with state-of-the-art sulfide superionic conductors such as $Li_7P_3S_{11}$, the LGPS family ($Li_{10}GeP_2S_{12}$ and $Li_{9.54}S_{1.74}P_{1.44}S_{11.7}C_{10.3}$, LYPS (undoped or doped) has slightly lower $Li^+$ conductivity. However, bulk ionic conductivity is no longer the critical factor in all-solid-state battery performance beyond 1 mS/cm. Indeed, other properties such as interfacial stability play a far more critical role. For instance, though the $Li_{9.54}Si_{1.74}P_{1.44}S_{11.7}Cl_{0.3}$ superionic conductor recently reported has an extraordinarily high room temperature ionic conductivity of 25 mS/cm, its interfacial stability is much poorer than the $Li_{9.6}P_3S_{12}$ composition in the same structure, which has a lower conductivity of ~1 mS/cm. The result is that $Li_4Ti_5O_{12}$, which has a voltage of 1.5 V against $Li/Li^+$, had to be used as the anode with $Li_{9.54}Si_{1.74}P_{1.44}S_{11.7}Cl_{0.3}$, lowering achievable energy densities due to the low overall operating voltage of ~2.5 V. In contrast, full cell performance at a relatively high operating voltage of up to 4.2 V was demonstrated for $Li_{9.6}P_3S_{12}$ with standard graphitic anodes.

LYPS compares favorably to these known superionic conductors in terms of both phase and electrochemical stability. The calculated $E_{hull}$ of LYPS is only 2 meV/atom, substantially lower than that of $Li_7P_3S_{11}$ (21 meV/atom), sion (in excess of 300%) at high lithiation, which may be detrimental to maintaining intimate electrode/electrolyte contact.

In summary, LYPS may present an overall better balance of properties as a lithium superionic conductor solid electrolyte for all-solid-state battery applications. It has clearly better predicted phase stability, and likely better interfacial stability based on the predicted phase equilibria at the electrode/electrolyte interface. Its conductivity, though somewhat lower than some of the state-of-the-art candidates, is sufficiently high that it is not likely to be a limiting factor, and can potentially be further improved with the demonstrated doping strategies.

Applications

Figure 9:
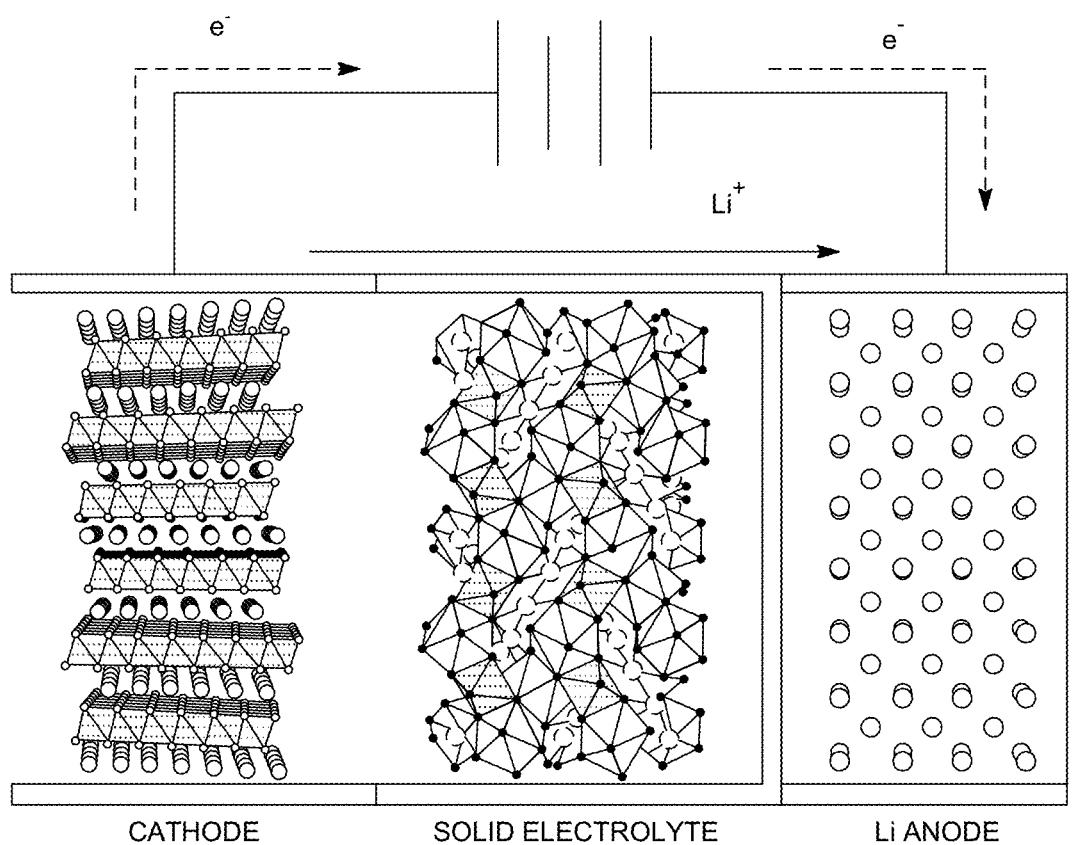
FIG. 9 is a schematic diagram of an all-solid-state lithium battery

Lithium superionic conductor electrolytes identified in accordance with the techniques described herein may be used in a variety of applications. For instance, they may be employed in a solid state battery. FIG. 9 is a schematic diagram of an all-solid-state lithium battery during a charge process. The battery contains three components: a metallic lithium anode, a charged cathode, and a lithium superionic conductor electrolyte. During the charge process, $Li^+$ ions are shuttled from cathode to anode through the solid electrolyte. The reverse procedure takes place during a discharge process.

Other Superionic Conductor Materials

Inspired by the similarity of the chemical space of Li—P—S and the recently identified superionic conductor Na—P—S as well as the prediction of $Li_3Y(PS_4)_2$ as described above as a new lithium superionic conductor electrolyte (SICE), we have conducted a high-throughput (HT) screening in Na-M-P—S chemical spaces for potential sodium SICEs. To increase the coverage of these chemical spaces, additional compounds substituted from existing A-M-P—X (A=Li, Na, Ag, K; X=S, O; M is non-redox-active element) chemical spaces are also included. From our calculations, we have identified one highly promising new sodium superionic conductor $Na_3Y(PS_4)_2$ for Na-ion battery applications.

Our system and method according to present principles can potentially address the safety issues caused by the use of organic liquid electrolytes in sodium ion batteries. The material is completely new in that no such structure is known in the literature. We predicted the new sodium superionic conductor $Na_3Y(PS_4)_2$ from density functional theory (DFT) calculations, and it has been subsequently synthesized and confirmed by X-ray diffraction (XRD) measurements. Based on our prediction, it should exhibit good phase stability, high $Na^+$ conductivity, low electronic conductivity and good electrochemical stability.

Figure 10:
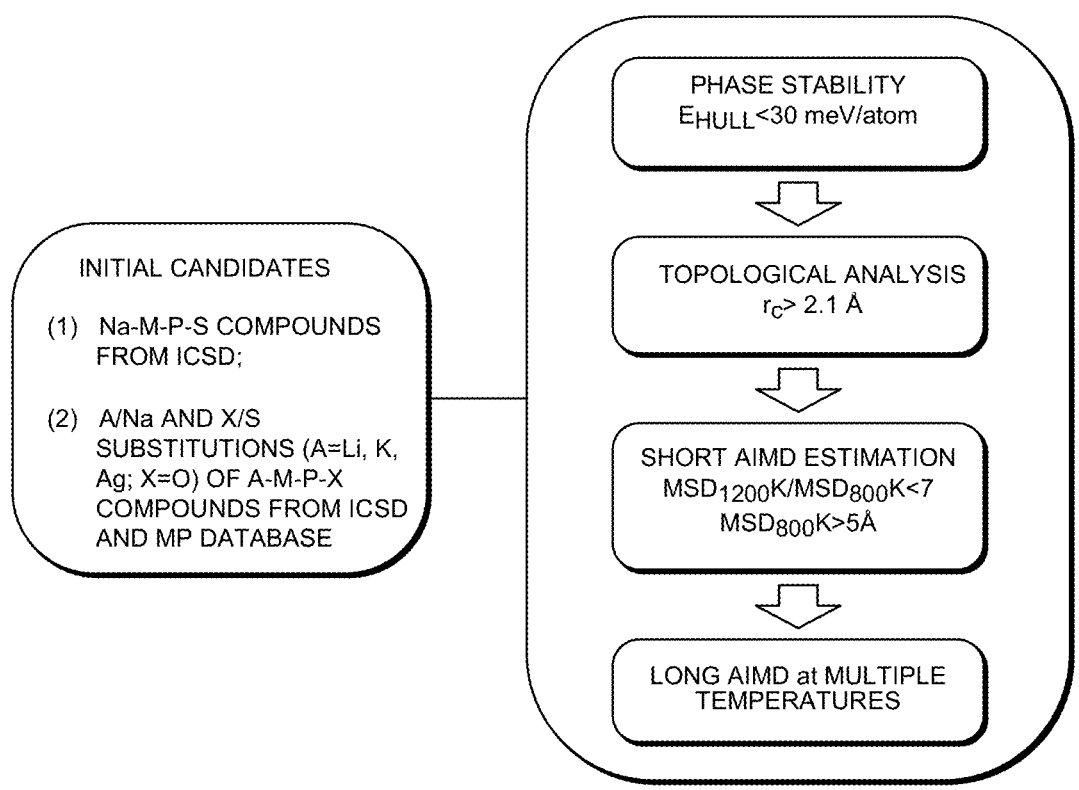
FIG. 10 is a flowchart of the screening procedure for new sodium superionic conductors.

The flow chart describing one example of a procedure of our first-principles high-throughput (HT) screening for superionic conductors is given in FIG. 10, which is similar to the flowchart shown in Figure for 1 for the procedure for identifying lithium superionic conductors.

Our initial candidate pool comprised two groups: (i) existing Na-M-P—S(M is non-redox-active elements) compounds from Inorganic Crystal Structure Databse (ICSD) 2016 version and (ii) A/Na, X/S substitution from A-M-P—X (A=Li, Na, Ag, K; X=S, O) chemical space. We first filtered out highly unstable materials (measured by $E_{hull}$; the higher the value, the more unstable a compound is) with $E_{hull}$>30 meV/atom. This is followed by a three-step diffusivity screening process. This screening procedure involves a topological analysis excluding those have too small or only 1D Li diffusion channels, a new short AIMD estimation process from two aspects of consideration (baseline diffusivity and activation energy) and a converged long-term AIMD simulation at multiple temperatures. The detailed cutoffs of the criteria are modified from our previous published work for Li superionic conductors (*Chem. Mater.* 29, 2474-2484 (2017)) due to the Li and Na ionic radius difference.

Figure 11:
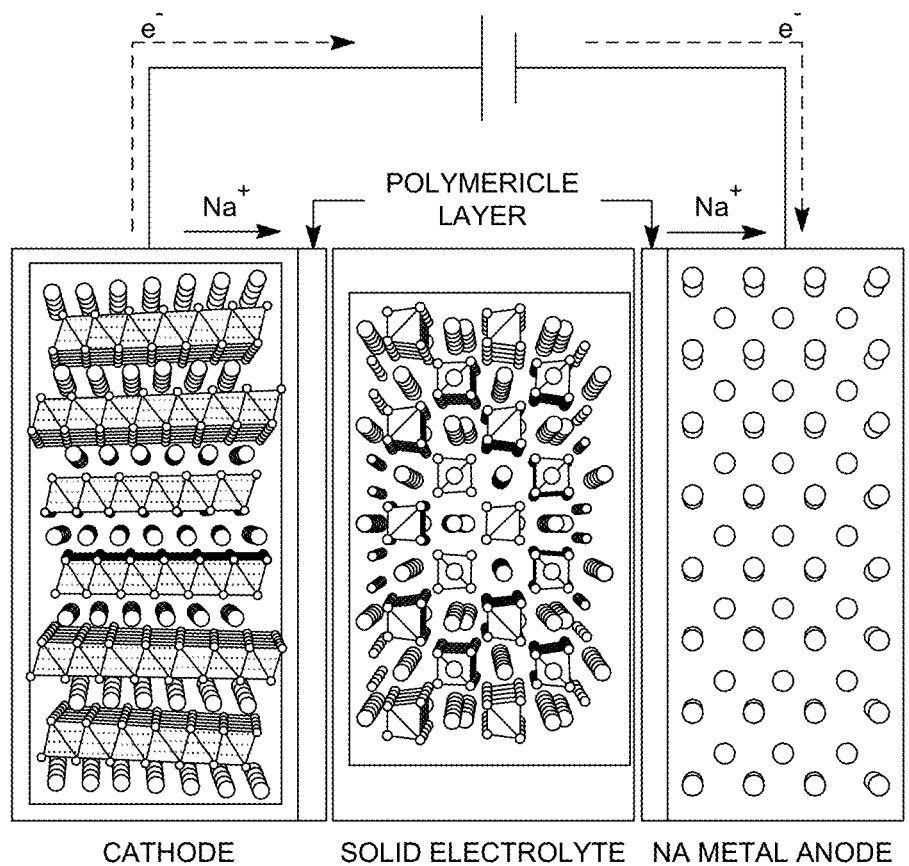
FIG. 11 is schematic diagram of an all-solid-state Na-ion battery.

FIG. 11 is the working schematics of a Na-ion battery. Anode, cathode and solid electrolyte are three components of the all-solid-state battery. During charging process, $Na^+$ ions are transported from cathode to anode through electrolytes. The reverse procedure happens at discharge process.

Because of the rareness of sodium superionic conductors and more requirements not only limited to conductivity, it is important to search for new sodium solid electrolytes with a combination of good phase stability, electronic conductivity and electrochemical stability. This motivates our first-principles guided new sodium superionic conductors investigation. There are three main stages during the development of our system and method according to present principles.

(i) Concept stage: We used our modified HT screening strategy to search for good sodium superionic conductors and predicted new $Na_3Y(PS_4)_2$ materials with good phase stability and excellent $Na^+$ conductivity. This computational work was followed by experimental synthesis attempts, which can verify the theoretical prediction and form a complete computational guided new material discovery chain.

Figure 12:
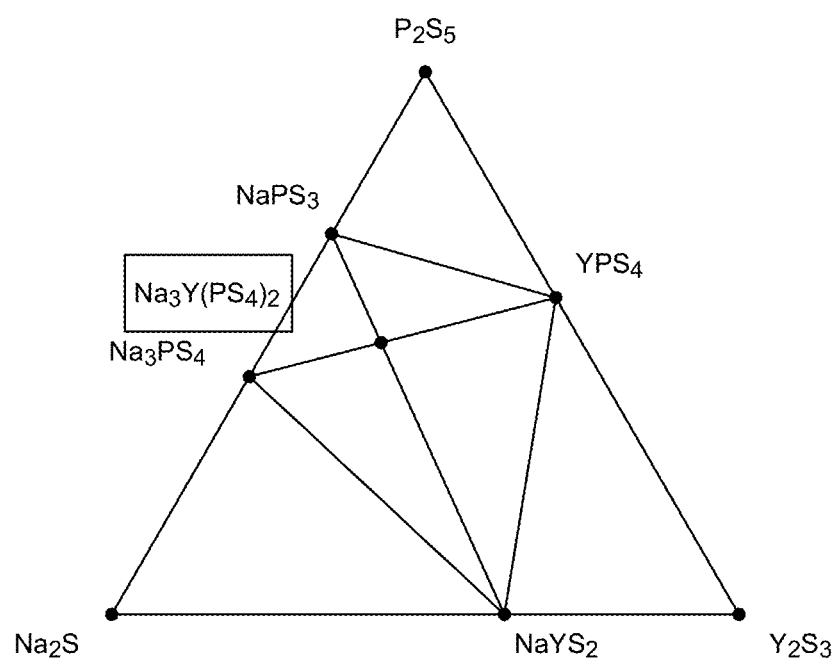
FIG. 12 shows the computed $Na_2S$—$P_2S_5$—$Y_2S_3$ phase diagram.

(ii) Computer modeling simulation stage: The first-principles high throughput screening approach shown in FIG. 10 is developed to search for the promising sodium conductors. Taking the great advantages of the robust computational method, we have investigated and developed several chemical spaces which are less studied before and FIG. 12 gives the phase diagram that we newly contributed to estimate the phase stability of $Na_3Y(PS_4)_2$ (the circular dots are all stable phases in the $Na_2S$—$P_2S_5$—$Y_2S_3$ phase diagram).

Figure 13:
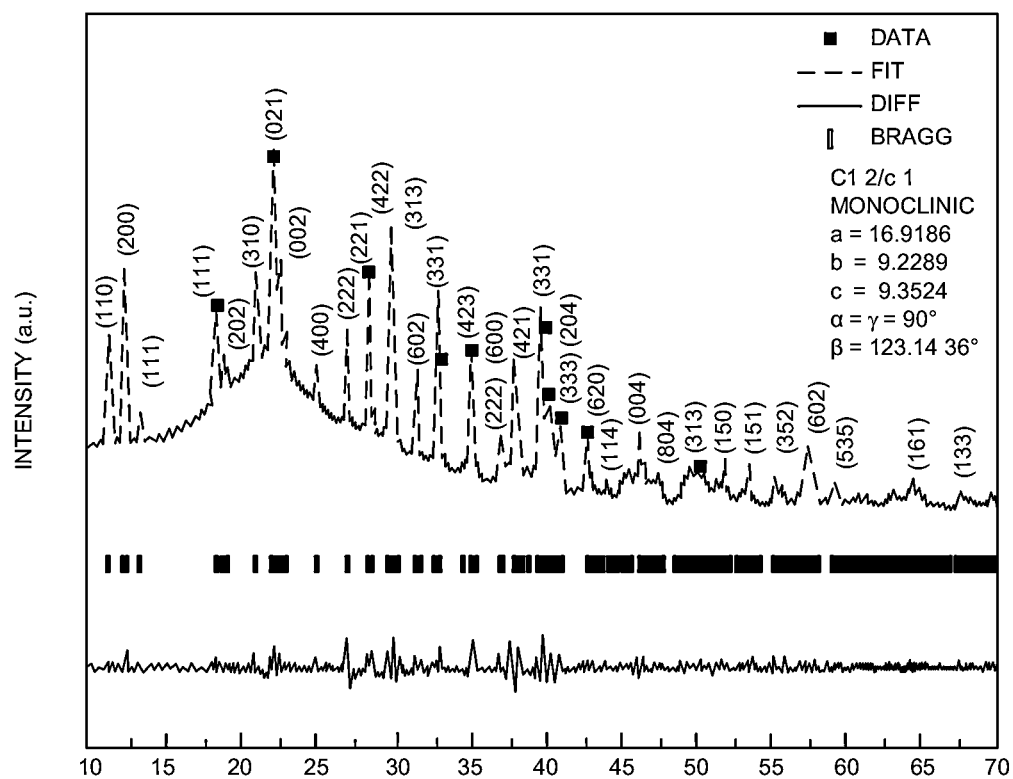
FIG. 13 shows XRD patterns of $Ag_3Y(PS_4)_2$.
Figure 14:
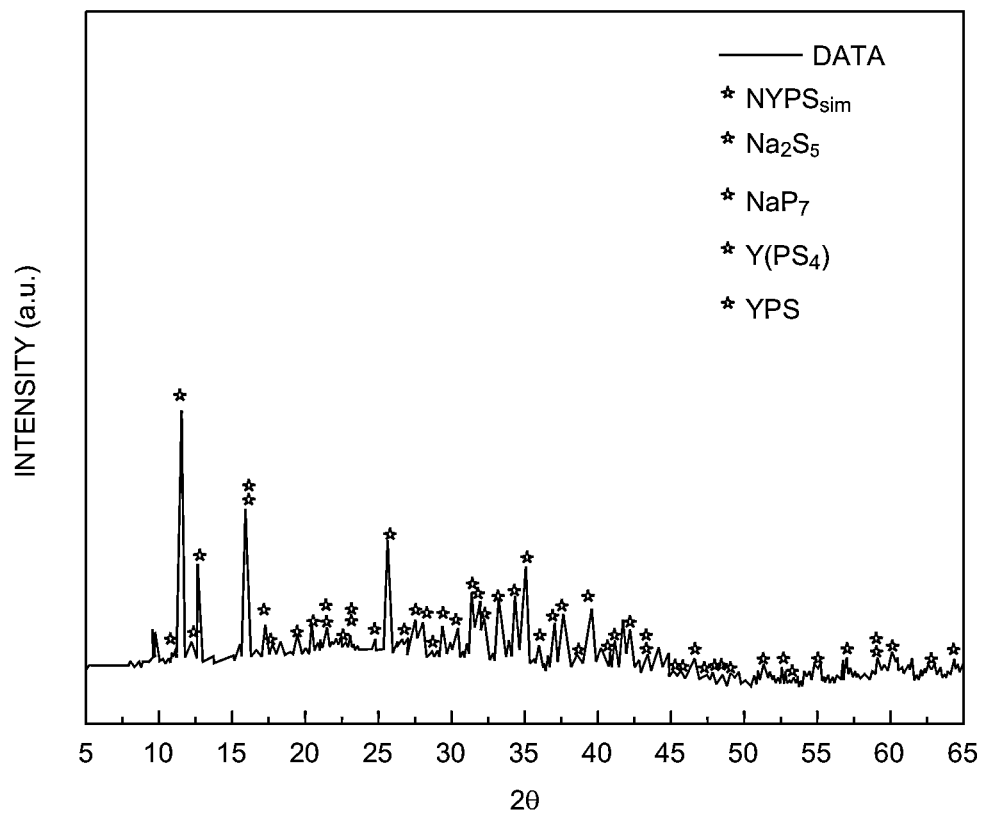
FIG. 14 shows preliminary XRD result of $Na_3Y(PS_4)_2$.

(iii) Experimental data stage: We have successfully reproduced the pure $Ag_3Y(PS_4)_2$ phase (XRD patterns shown in FIG. 13). New $Na_3Y(PS_4)_2$ material has already been synthesized and XRD results show the signal peaks of this new compound (FIG. 14).

Rechargeable Na-ion batteries have enjoyed significant attention and interest in recent years due to the abundant sodium resources and more possible new chemistries. As the key component of all-solid-state batteries, sodium solid electrolytes overcome the leakage and flammable problem caused by organic liquid electrolytes. For commercial application, a combination of multiple properties should be taken into consideration. The promising material we predicted ($Na_3Y(PS_4)_2$) has sufficiently high conductivity (>10 mS/cm) and good phase stability as well as electrochemical stability. Our computational guided new material discovery strategy can greatly speed up the procedure of searching for promising candidates and reduce the efforts in experiments.

Experimental achievement also verifies the validation of our HT screening method.

What is claimed is:

1. A high-throughput screening method for identifying superionic conductors, comprising:
   a. determining an initial pool of Na-based candidate structures that are analogs to existing A-M-P—X quaternary structures, where A is Li, Ag, Na, or K, M is a non-redox active element, and X is S or O;
   b. filtering out unstable candidate structures; and
   c. performing diffusivity screening on remaining candidate structures.

2. The method of claim 1, wherein the filtering is performed by phase stability analysis.

3. The method of claim 1, wherein the diffusivity screening is performed by a three step approach.

4. The method of claim 3, wherein the three steps include topological analysis to exclude candidate structures having only 1D Li diffusion pathways, quick diffusivity estimation, and long ab initio molecular dynamics (AIMD) simulations.

5. The method of claim 4, wherein the long AIMD simulations are performed at multiple temperatures for a converged diffusivity of the most promising candidates.

6. The method of claim 5, further comprising performing dopant and composition optimization.

7. The method of claim 3, wherein the quick diffusivity estimation uses mean square displacement from short ab initio molecular dynamics (AIMD) simulations.

8. A superionic conductor, identified by the method of claim 1.

9. The superionic conductor of claim 8, having the structure of $Na_3Y(PS_4)_2$.

* * * * *